(12) United States Patent
Liu et al.

(10) Patent No.: US 8,754,069 B2
(45) Date of Patent: Jun. 17, 2014

(54) BETULINIC ACID DERIVATIVES WITH ANTIVIRAL ACTIVITY

(71) Applicant: Bristol-Myers Squibb Company, Princeton, NJ (US)

(72) Inventors: Zheng Liu, Beacon Falls, CT (US); Nicholas A. Meanwell, East Hampton, CT (US); Alicia Regueiro-Ren, Middletown, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/623,165

(22) Filed: Sep. 20, 2012

(65) Prior Publication Data

US 2013/0072465 A1   Mar. 21, 2013

Related U.S. Application Data

(60) Provisional application No. 61/537,099, filed on Sep. 21, 2011.

(51) Int. Cl.
*A61K 31/58* (2006.01)
*A61K 31/56* (2006.01)
*C07J 53/00* (2006.01)

(52) U.S. Cl.
USPC ............. 514/176; 514/182; 540/47; 552/510

(58) Field of Classification Search
USPC ...................... 540/47; 552/510; 514/176, 182
See application file for complete search history.

(56) References Cited

U.S. PATENT DOCUMENTS

| | | | |
|---|---|---|---|
| 5,413,999 | A | 5/1995 | Vacca et al. |
| 5,679,828 | A | 10/1997 | Lee et al. |
| 7,354,924 | B2 | 4/2008 | Wang et al. |
| 7,365,221 | B2 | 4/2008 | Allaway et al. |
| 7,745,625 | B2 | 6/2010 | Ueda et al. |
| 2005/0239748 | A1 | 10/2005 | Power et al. |
| 2008/0207573 | A1 | 8/2008 | Yager et al. |
| 2012/0142653 | A1 | 6/2012 | Regueiro-Ren et al. |
| 2012/0142707 | A1 | 6/2012 | Regueiro-Ren et al. |
| 2013/0029954 | A1 | 1/2013 | Regueiro-Ren et al. |
| 2013/0035318 | A1 | 2/2013 | Regueiro-Ren et al. |

FOREIGN PATENT DOCUMENTS

| | | |
|---|---|---|
| WO | WO 98/51293 | 11/1998 |
| WO | WO 98/51294 | 11/1998 |
| WO | WO 2004/089357 | 10/2004 |
| WO | WO 2006/053255 | 5/2006 |
| WO | WO 2008/127364 | 10/2008 |
| WO | WO 2009/100532 | 8/2009 |
| WO | WO 2011/007230 | 1/2011 |

OTHER PUBLICATIONS

Blair, W.S. et al., "HIV-1 entry—an expanding portal for drug discovery", Drug Discovery Today, vol. 5, No. 5, pp. 183-194 (2000).
Hotoda, H., "Small-molecule inhibitors of HIV-1 entry via chemokine receptors", Drugs of the Future, vol. 24, No. 12, pp. 1355-1362 (1999).
Kashiwada, Y. et al., "Betulinic Acid and Dihydrobetulinic Acid Derivatives as Potent Anti-HIV Agents", Journal of Medicinal Chemistry, vol. 39, No. 5, pp. 1016-1017 (1996).
Meanwell, N.A. et al., "Inhibitors of the entry of HIV into host cells", Current Opinion in Drug Discovery & Development, vol. 6, No. 4, pp. 451-461 (2003).
Pokrovskii, A.G. et al., "Synthesis of derivatives of plant triterpenes and study of their antiviral and immunostimulating activity", Khimiya y Interesakh Ustoichivogo Razvitiya, vol. 9, No. 3, pp. 485-491 (2001) (English abstract).
Sodroski, J.G., "HIV-1 Entry Inhibitors in the Side Pocket: Minireview", Cell, vol. 99, pp. 243-246 (1999).
Zhu, Y.-M. et al., "Synthesis and Anti-HIV Activity of Oleanolic Acid Derivatives", Bioorganic & Medicinal Chemistry Letters, vol. 11, pp. 3115-3118 (2001).
Swidorski et al., U.S. Appl. No. 13/760,726, filed Feb. 6, 2013.

*Primary Examiner* — Barbara P Badio
(74) *Attorney, Agent, or Firm* — John F. Levis

(57) ABSTRACT

Compounds of Formula I:

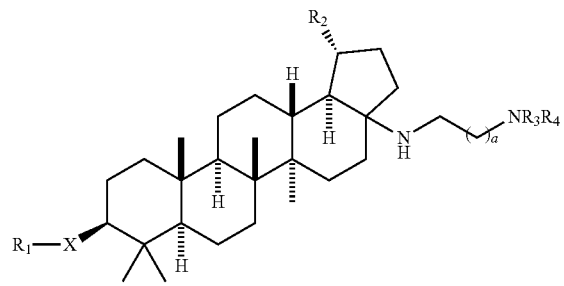

Formula I that possess unique antiviral activity are provided as HIV maturation inhibitors. These compounds are useful for the treatment of HIV and AIDS.

10 Claims, No Drawings

BETULINIC ACID DERIVATIVES WITH ANTIVIRAL ACTIVITY

CROSS REFERENCE TO RELATED APPLICATION

This non-provisional application claims the benefit of U.S. Provisional Application Ser. No. 61/537,099 filed Sep. 21, 2011.

FIELD OF THE INVENTION

The present invention relates to novel compounds useful against HIV and, more particularly, to compounds derived from betulinic acid and other structurally-related compounds which are useful as HIV maturation inhibitors, and to pharmaceutical compositions containing same, as well as to methods for their preparation.

BACKGROUND OF THE INVENTION

HIV-1 (human immunodeficiency virus -1) infection remains a major medical problem, with an estimated 45-50 million people infected worldwide at the end of 2010. The number of cases of HIV and AIDS (acquired immunodeficiency syndrome) has risen rapidly. In 2005, approximately 5.0 million new infections were reported, and 3.1 million people died from AIDS. Currently available drugs for the treatment of HIV include nucleoside reverse transcriptase (RT) inhibitors or approved single pill combinations: zidovudine (or AZT or RETROVIR®), didanosine (or VIDEX®), stavudine (or ZERIT®), lamivudine (or 3TC or EPIVIR®), zalcitabine (or DDC or HIVID®), abacavir succinate (or ZIAGEN®), Tenofovir disoproxil fumarate salt (or VIREAD®), emtricitabine (or FTC EMTRIVA®), COMBIVIR® (contains -3TC plus AZT), TRIZIVIR® (contains abacavir, lamivudine, and zidovudine), EPZICOM® (contains abacavir and lamivudine), TRUVADA® (contains VIREAD® and EMTRIVA®); non-nucleoside reverse transcriptase inhibitors: rilpivirine (or EDURANT®), nevirapine (or VIRAMUNE°), delavirdine (or RESCRIPTOR®) and efavirenz (or SUSTIVA°), ATRIPLA® (TRUVADA®+SUSTIVA®), COMPLERA® (TRUVADA®+EDURANT®), and etravirine, and peptidomimetic protease inhibitors or approved formulations: saquinavir, indinavir, ritonavir, nelfinavir, amprenavir, lopinavir, KALETRA® (lopinavir and Ritonavir), darunavir, atazanavir (REYATAZ®) and tipranavir (APTIVUS®), and integrase inhibitors such as raltegravir (ISENTRESS®), and entry inhibitors such as enfuvirtide (T-20) (FUZEON®) and maraviroc (SELZENTRY®).

Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients may ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present. Therefore, novel anti-HIV agents exhibiting distinct resistance patterns, and favorable pharmacokinetic as well as safety profiles are needed to provide more treatment options. Improved HIV fusion inhibitors and HIV entry coreceptor antagonists are two examples of new classes of anti-HIV agents further being studied by a number of investigators.

HIV attachment inhibitors are a further subclass of antiviral compounds that bind to the HIV surface glycoprotein gp120, and interfere with the interaction between the surface protein gp120 and the host cell receptor CD4. Thus, they prevent HIV from attaching to the human CD4 T-cell, and block HIV replication in the first stage of the HIV life cycle. The properties of HIV attachment inhibitors have been improved in an effort to obtain compounds with maximized utility and efficacy as antiviral agents. In particular, U.S. Pat. No. 7,354,924 and US 2005/0209246 are illustrative of HIV attachment inhibitors.

Another emerging class of compounds for the treatment of HIV are called HIV maturation inhibitors. Maturation is the last of as many as 10 or more steps in HIV replication or the HIV life cycle, in which HIV becomes infectious as a consequence of several HIV protease-mediated cleavage events in the gag protein that ultimately results in release of the capsid (CA) protein. Maturation inhibitors prevent the HIV capsid from properly assembling and maturing, from forming a protective outer coat, or from emerging from human cells. Instead, non-infectious viruses are produced, preventing subsequent cycles of HIV infection.

Certain derivatives of betulinic acid have now been shown to exhibit potent anti-HIV activity as HIV maturation inhibitors. For example, U.S. Pat. No. 7,365,221 discloses monoacylated betulin and dihydrobetuline derivatives, and their use as anti-HIV agents. As discussed in the '221 reference, esterification of betulinic acid (1) with certain substituted acyl groups, such as 3',3'-dimethylglutaryl and 3',3'-dimethylsuccinyl groups produced derivatives having enhanced activity (Kashiwada, Y., et al., J. Med. Chem. 39:1016-1017 (1996)). Acylated betulinic acid and dihydrobetulinic acid derivatives that are potent anti-HIV agents are also described in U.S. Pat. No. 5,679,828. Esterification of the hydroxyl in the 3 carbon of betulin with succinic acid also produced a compound capable of inhibiting HIV-1 activity.

Other references to the use of treating HIV infection with compounds derived from betulinic acid include US 2005/0239748 and US 2008/0207573, as well as WO2006/053255, WO2009/100532 and WO2011/007230.

One HIV maturation compound that has been in development has been identified as Bevirimat or PA-457, with the chemical formula of $C_{36}H_{56}O_6$ and the IUPAC name of 3β-(3-carboxy-3-methyl-butanoyloxy) lup-20(29)-en-28-oic acid.

Reference is also made herein to the applications by Bristol-Myers Squibb entitled "MODIFIED C-3 BETULINIC ACID DERIVATIVES AS HIV MATURATION INHIBITORS" U.S. Ser. No. 13/151,706 filed on Jun. 2, 2011 (US 20120142707A1) and "C-28 AMIDES OF MODIFIED C-3 BETULINIC ACID DERIVATIVES AS HIV MATURATION INHIBITORS" U.S. Ser. No. 13/151,722, filed on Jun. 2, 2011 (US20120142653A1). Reference is also made to the applications entitled "C-28 AMINES OF C-3 MODIFIED BETULINIC ACID DERIVATIVES AS HIV MATURATION INHIBITORS" U.S. Ser. No. 13/359,680, filed on Jan. 27, 2012, and "C-17 AND C-3 MODIFIED TRITERPENOIDS WITH HIV MATURATION INHIBITORY ACTIVITY" U.S. Ser. No. 13/359,727, filed on Jan. 27, 2012.

What is now needed in the art are new compounds which are useful as HIV maturation inhibitors, as well as new pharmaceutical compositions containing these compounds.

SUMMARY OF THE INVENTION

The present invention provides compounds of Formula I below, including pharmaceutically acceptable salts thereof, their pharmaceutical formulations, and their use in patients suffering from or susceptible to a virus such as HIV. The compounds of Formula I are effective antiviral agents, particularly as inhibitors of HIV. They are useful for the treatment of HIV and AIDS.

One embodiment of the present invention is directed to a compound of Formula I, including pharmaceutically acceptable salts thereof:

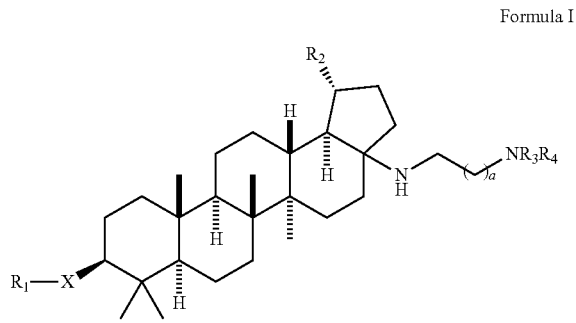

Formula I wherein a is 1 to 4;
X is —O—;
$R_1$ is —C(O)CH$_2$C(CH$_3$)$_2$COOH, —C(O)C(CH$_3$)$_2$CH$_2$COOH, or —C(O)CH$_2$C(CH$_3$)$_2$CH$_2$COOH;
$R_2$ is selected from the group of —H, methyl, isopropenyl and isopropyl;
$R_3$ and $R_4$ are independently selected from the group of —H, —C$_{1-6}$ alkyl, —C$_{1-6}$ alkylsubstituted alkyl and —C$_{3-6}$ cycloalkyl;
or $R_3$ and $R_4$ are taken together with the adjacent N to form a cycle selected from the group of:

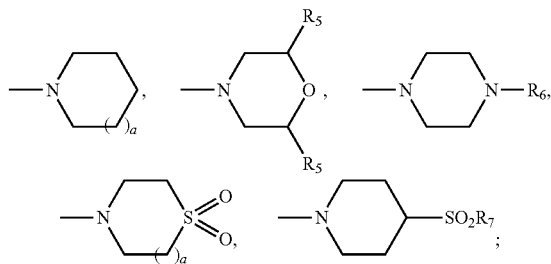

$R_5$ is independently —H or —C$_{1-6}$ alkyl;
$R_6$ is selected from the group of —SO$_2$R$_7$, —SO$_2$NR$_8$R$_9$
$R_7$ is selected from the group of —C$_{1-6}$ alkyl, —C$_{1-6}$ alkylsubstituted alkyl, —C$_{3-6}$ cycloalkyl and aryl; and
$R_8$ and $R_9$ are independently selected from the group of —H, —C$_{1-6}$ alkyl, and —C$_{1-6}$ alkylsubstituted alkyl.

In a further embodiment, there is provided a method for treating mammals infected with a virus, especially wherein said virus is HIV, comprising administering to said mammal an antiviral effective amount of a compound of Formula I above, and one or more pharmaceutically acceptable carriers, excipients or diluents. Optionally, the compound of Formula I can be administered in combination with an antiviral effective amount of another AIDS treatment agent selected from the group consisting of: (a) an AIDS antiviral agent; (b) an anti-infective agent; (c) an immunomodulator; and (d) other HIV entry inhibitors.

Another embodiment of the present invention is a pharmaceutical composition comprising an antiviral effective amount of a compound of Formula I, and one or more pharmaceutically acceptable carriers, excipients, and diluents; and optionally in combination with an antiviral effective amount of another AIDS treatment agent selected from the group consisting of: (a) an AIDS antiviral agent; (b) an anti-infective agent; (c) an immunomodulator; and (d) other HIV entry inhibitors.

In another embodiment of the invention there is provided one or more methods for making the compounds of Formula I.

Also provided herein are intermediate compounds useful in making the compounds of Formula I.

The present invention is directed to these, as well as other important ends, hereinafter described.

DETAILED DESCRIPTION OF THE EMBODIMENTS

Since the compounds of the present invention may possess asymmetric centers and therefore occur as mixtures of diastereomers and enantiomers, the present disclosure includes the individual diastereoisomeric and enantiomeric forms of the compounds of Formula I, in addition to the mixtures thereof.

Definitions

Unless otherwise specifically set forth elsewhere in the application, one or more of the following terms may be used herein, and shall have the following meanings:

"H" refers to hydrogen, including its isotopes, such as deuterium.

The term "C$_{1-6}$ alkyl" as used herein and in the claims (unless specified otherwise) mean straight or branched chain alkyl groups such as methyl, ethyl, propyl, isopropyl, butyl, isobutyl, t-butyl, amyl, hexyl and the like.

"C$_1$-C$_4$ fluoroalkyl" refers to F-substituted C$_1$-C$_4$ alkyl wherein at least one H atom is substituted with F atom, and each H atom can be independently substituted by F atom;

"Halogen" refers to chlorine, bromine, iodine or fluorine.

An "aryl" or "Ar" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthalenyl and anthracenyl. The aryl group may be substituted or unsubstituted. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —NR$^x$R$^y$, wherein R$^x$ and R$^y$ are independently selected from the group consisting of hydrogen, alkyl, cycloalkyl, aryl, carbonyl, C-carboxy, sulfonyl, trihalomethyl, and, combined, a five- or six-member heteroalicyclic ring.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl. diazinyl, pyrazine, triazinyl, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thioalkoxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —$NR^xR^y$, wherein $R^x$ and $R^y$ are as defined above.

As used herein, a "heteroalicyclic" group refers to a monocyclic or fused ring group having in the ring(s) one or more atoms selected from the group consisting of nitrogen, oxygen and sulfur. Rings are selected from those which provide stable arrangements of bonds and are not intended to encompass systems which would not exist. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —$NR^xR^y$, wherein $R^x$ and $R^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexene, cycloheptane, cycloheptene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, amidino, guanidino, ureido, phosphonyl, amino and —$NR^xR^y$ with $R^x$ and $R^y$ as defined above.

An "alkenyl" group refers to an alkyl group, as defined herein, having at least two carbon atoms and at least one carbon-carbon double bond.

An "alkynyl" group refers to an alkyl group, as defined herein, having at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "Keto" group refers to a —CC(=O)C— group wherein the carbon on either or both sides of the C=O may be alkyl, cycloalkyl, aryl or a carbon of a heteroaryl or heteroalicyclic group.

A "trihalomethanecarbonyl" group refers to a $Z_3CC$(=O)— group with said Z being a halogen.

A "C-carboxy" group refers to a —C(=O)O—R" groups, with R" as defined herein.

An "O-carboxy" group refers to a R"C(—O)O-group, with R" as defined herein.

A "carboxylic acid" group refers to a C-carboxy group in which R" is hydrogen.

A "trihalomethyl" group refers to a —$CZ_3$, group wherein Z is a halogen group as defined herein.

A "trihalomethanesulfonyl" group refers to an $Z_3CS$(=O)$_2$— groups with Z as defined above.

A "trihalomethanesulfonamido" group refers to a $Z_3CS(=O)_2NR^x$— group with Z as defined above and $R^x$ being H or $(C_{1-6})$alkyl.

A "sulfinyl" group refers to a —S(=O)—R" group, with R" being $(C_{1-6})$alkyl.

A "sulfonyl" group refers to a —S(=O)$_2$R" group with R" being $(C_{1-6})$alkyl.

A "S-sulfonamido" group refers to a —S(=O)$_2$NR$^X$R$^Y$, with $R^X$ and $R^Y$ independently being H or $(C_{1-6})$alkyl.

A "N-Sulfonamido" group refers to a R"S(=O)$_2$NR$_X$— group, with $R_x$ being H or $(C_{1-6})$alkyl.

A "O-carbamyl" group refers to a —OC(=O)NR$^x$R$^y$ group, with $R^X$ and $R^Y$ independently being H or $(C_{1-6})$alkyl.

A "N-carbamyl" group refers to a R$^x$OC(=O)NR$^y$ group, with $R^x$ and $R^y$ independently being H or $(C_{1-6})$alkyl.

A "O-thiocarbamyl" group refers to a —OC(=S)NR$^x$R$^y$ group, with $R^x$ and $R^y$ independently being H or $(C_{1-6})$alkyl.

A "N-thiocarbamyl" group refers to a R$^x$OC(=S)NR$^y$— group, with $R^x$ and $R^y$ independently being H or $(C_{1-6})$alkyl.

An "amino" group refers to an —NH$_2$ group.

A "C-amido" group refers to a —C(=O)NR$^x$R$^y$ group, with $R^x$ and $R^y$ independently being H or $(C_{1-6})$alkyl.

A "C-thioamido" group refers to a —C(=S)NR$^x$R$^y$ group, with $R^x$ and $R^y$ independently being H or $(C_{1-6})$alkyl.

A "N-amido" group refers to a R$^x$C(=O)NR$^y$— group, with $R^x$ and $R^y$ independently being H or $(C_{1-6})$alkyl.

An "ureido" group refers to a —NR$^x$C(=O)NR$^y$R$^{y2}$ group, with $R^x$, $R^y$, and $R^{y2}$ independently being H or $(C_{1-6})$alkyl.

A "guanidino" group refers to a —R$^x$NC(=N)NR$^y$R$^{y2}$ group, with $R^x$, $R^y$, and $R^{y2}$ independently being H or $(C_{1-6})$alkyl.

A "amidino" group refers to a R$^x$R$^y$NC(=N)— group, with $R^x$ and $R^y$ independently being H or $(C_{1-6})$alkyl.

A "cyano" group refers to a —CN group.

A "silyl" group refers to a —Si(R")$_3$, with R" being $(C_{1-6})$ alkyl or phenyl.

A "phosphonyl" group refers to a P(=O)(OR$^x$)$_2$ with $R^x$ being $(C_{1-6})$alkyl.

A "hydrazino" group refers to a —NR$^x$NR$^x$R$^{y2}$ group, with $R^x$, $R^y$, and $R^{y2}$ independently being H or $(C_{1-6})$alkyl.

A "4, 5, or 6 membered ring cyclic N-lactam" group refers to

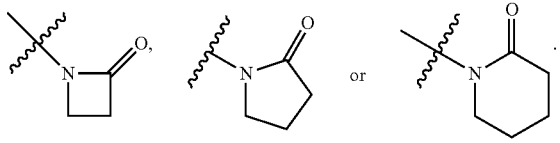 [SMILES: *N1CCC1=O ; *N1CCCC1=O ; *N1CCCCC1=O]

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present disclosure are based on the known general principles of chemical bonding. It is understood that the claims do not encompass structures known to be unstable or not able to exist based on the literature.

Pharmaceutically acceptable salts and prodrugs of compounds disclosed herein are within the scope of the invention.

The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

As stated above, the compounds of the invention also include "prodrugs". The term "prodrug" as used herein encompasses both the term "prodrug esters" and the term "prodrug ethers". The term "prodrug esters" as employed herein includes esters and carbonates formed by reacting one or more hydroxyls of compounds of Formula I with either alkyl, alkoxy, or aryl substituted acylating agents or phosphorylating agent employing procedures known to those skilled in the art to generate acetates, pivalates, methylcarbonates, benzoates, amino acid esters, phosphates, half acid esters such as malonates, succinates or glutarates, and the like. In certain embodiments, amino acid esters may be especially preferred.

As set forth above, the invention is directed to compounds of Formula I, including pharmaceutically acceptable salts thereof:

Formula I

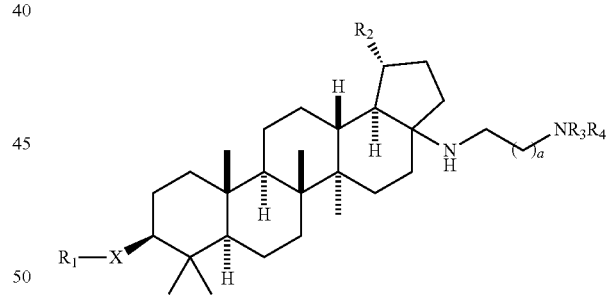

wherein a is 1 to 4;

X is —O;

$R_1$ is —C(O)CH$_2$C(CH$_3$)$_2$COOH, —C(O)C(CH$_3$)$_2$CH$_2$COOH, or —C(O)CH$_2$C(CH$_3$)$_2$CH$_2$COOH;

$R_2$ is selected from the group of —H, methyl, isopropenyl and isopropyl;

$R_3$ and $R_4$ are independently selected from the group of —H, —C$_{1-6}$ alkyl, —C$_{1-6}$ alkylsubstituted alkyl and —C$_{3-6}$ cycloalkyl;

or $R_3$ and $R_4$ are taken together with the adjacent N to form a cycle selected from the group of:

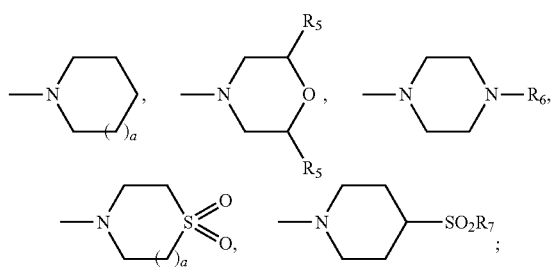

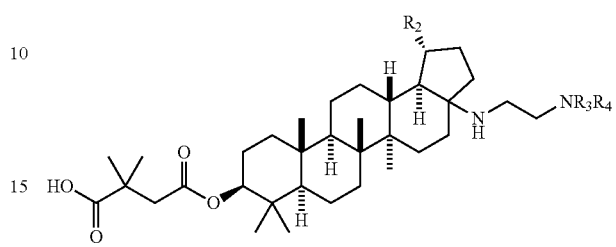

$R_5$ is independently —H or —$C_{1-6}$ alkyl;

$R_6$ is selected from the group of —$SO_2R_7$, —$SO_2NR_8R_9$ $R_7$ is selected from the group of —$C_{1-6}$ alkyl, —$C_{1-6}$ alkyl-substituted alkyl, —$C_{3-6}$ cycloalkyl and aryl; and $R_8$ and $R_9$ are independently selected from the group of —H, —$C_{1-6}$ alkyl, and —$C_{1-6}$ alkylsubstituted alkyl.

More preferred compounds of Formula I include those wherein a is 1.

Also preferred are compounds wherein $R_1$ is —C(O)$CH_2$C($CH_3$)$_2$COOH.

A preferred compound of Formula I has the structural formula:

Other compounds which are preferred as part of the invention include the following:

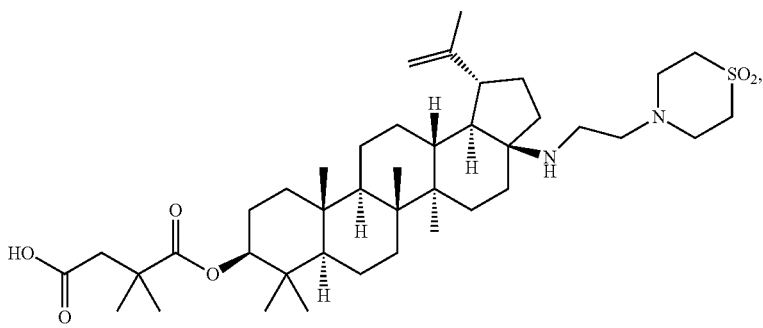

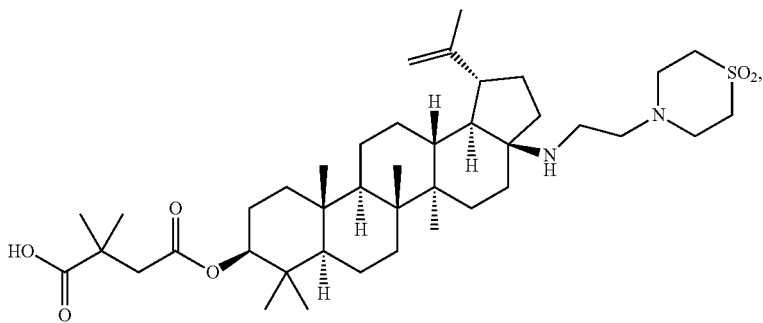

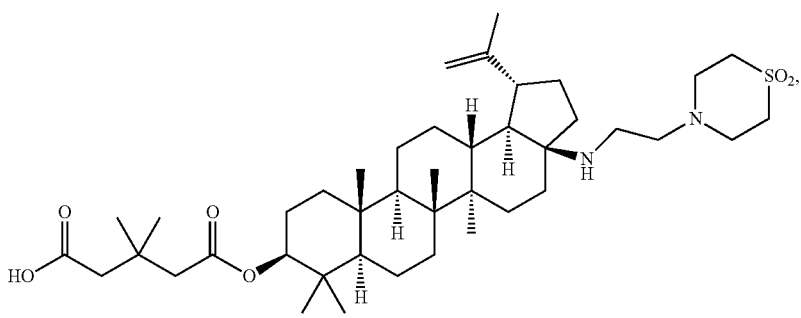

-continued
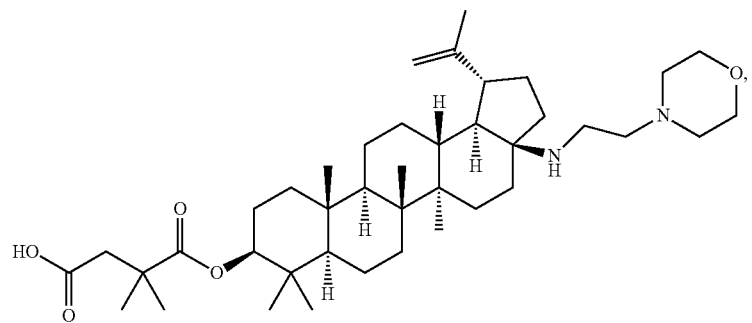
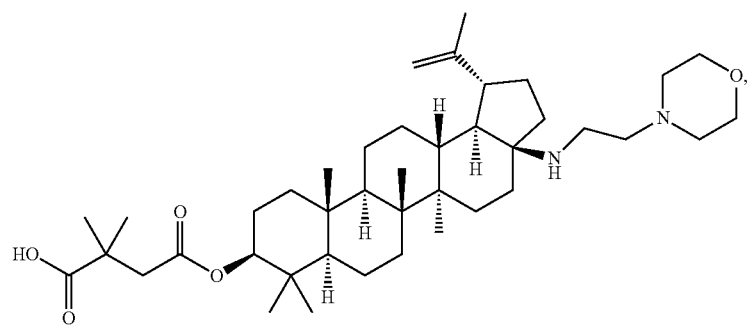
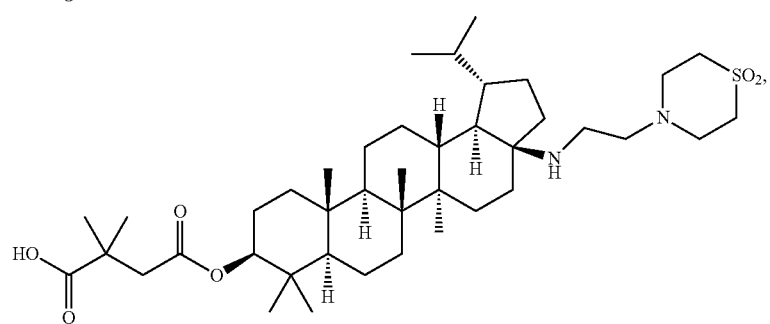
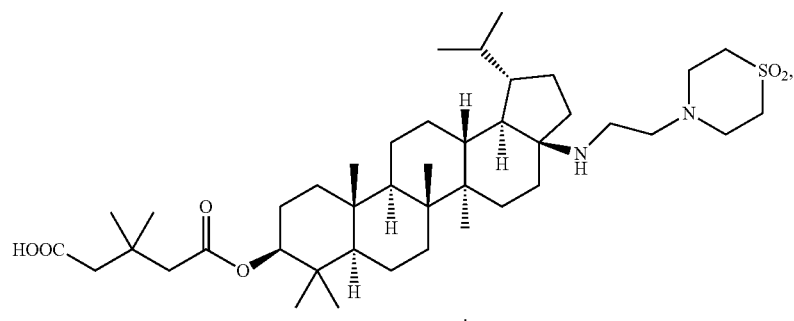
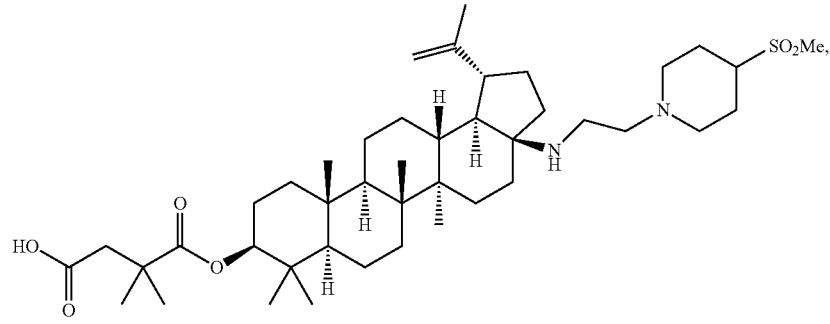

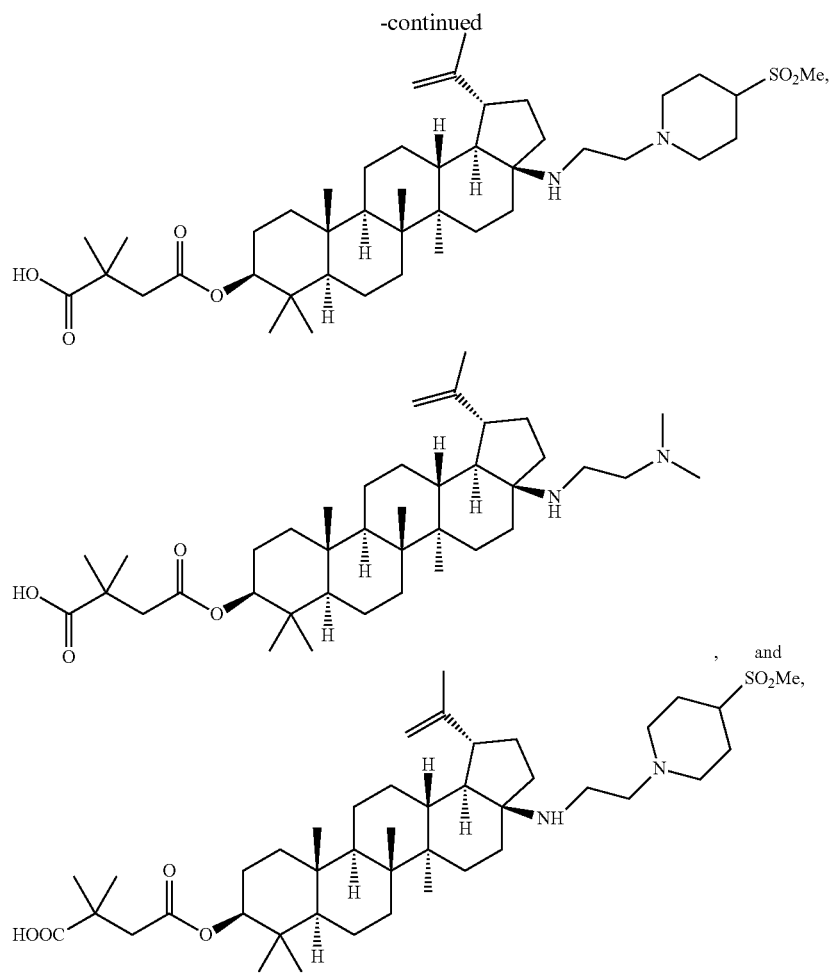

including pharmaceutically acceptable salts thereof.

The compounds of the present invention, according to all the various embodiments described above, may be administered orally, parenterally (including subcutaneous injections, intravenous, intramuscular, intrasternal injection or infusion techniques), by inhalation spray, or rectally, and by other means, in dosage unit formulations containing non-toxic pharmaceutically acceptable carriers, excipients and diluents available to the skilled artisan. One or more adjuvants may also be included.

Thus, in accordance with the present invention, there is further provided a method of treatment, and a pharmaceutical composition, for treating viral infections such as HIV infection and AIDS. The treatment involves administering to a patient in need of such treatment a pharmaceutical composition which contains an antiviral effective amount of one or more of the compounds of Formula I, together with one or more pharmaceutically acceptable carriers, excipients or diluents. As used herein, the term "antiviral effective amount" means the total amount of each active component of the composition and method that is sufficient to show a meaningful patient benefit, i.e., inhibiting, ameliorating, or healing of acute conditions characterized by inhibition of the HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing, ameliorating or healing diseases associated with HIV infection.

The pharmaceutical compositions of the invention may be in the form of orally administrable suspensions or tablets; as well as nasal sprays, sterile injectable preparations, for example, as sterile injectable aqueous or oleaginous suspensions or suppositories. Pharmaceutically acceptable carriers, excipients or diluents may be utilized in the pharmaceutical compositions, and are those utilized in the art of pharmaceutical preparations.

When administered orally as a suspension, these compositions are prepared according to techniques typically known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds herein set forth can be administered orally to humans in a dosage range of about 1 to 100 mg/kg body weight in divided doses, usually over an extended period, such as days, weeks, months, or even years. One preferred dosage range is about 1 to 10 mg/kg body weight orally in divided doses. Another preferred dosage range is about 1 to 20 mg/kg body weight in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Also contemplated herein are combinations of the compounds of Formula I herein set forth, together with one or more other agents useful in the treatment of AIDS. For example, the compounds of this disclosure may be effectively administered, whether at periods of pre-exposure and/or post-exposure, in combination with effective amounts of the AIDS antivirals, immunomodulators, antiinfectives, or vaccines, such as those in the following non-limiting table:

| Drug Name | Manufacturer | Indication |
|---|---|---|
| ANTIVIRALS | | |
| 097 | Hoechst/Bayer | HIV infection, AIDS, ARC (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Darunavir | Tibotec-J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266, SUSTIVA ®) (-)6-Chloro-4-(S)-cyclopropylethynyl-4(S)-trifluoro-methy1-1,4-dihydro-2H-3,1-benzoxazin-2-one, STOCRINE | Bristol Myers Squibb | HIV infection, AIDS, ARC (non-nucleoside RT inhibitor) |
| EL10 | Elan Corp, PLC (Gainesville, GA) | HIV infection |
| Etravirine | Tibotec/J & J | HIV infection, AIDS, ARC (non-nucleoside reverse transcriptase inhibitor) |
| Famciclovir | Smith Kline | herpes zoster, herpes simplex |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |

-continued

| Drug Name | Manufacturer | Indication |
|---|---|---|
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Rilpivirine | Tibotec | HIV infection, AIDS, ARC (NNRTI) |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (VIREAD ®) | Gilead | HIV infection, AIDS, (reverse transcriptase inhibitor) |
| EMTRIVA ® (Emtricitabine) (FTC) | Gilead | HIV infection, AIDS, (reverse transcriptase inhibitor) |
| COMBIVIR ® | GSK | HIV infection, AIDS, (reverse transcriptase inhibitor) |
| Abacavir succinate (or ZIAGEN ®) | GSK | HIV infection, AIDS, (reverse transcriptase inhibitor) |
| REYATAZ ® (or atazanavir) | Bristol-Myers Squibb | HIV infection AIDs, protease inhibitor |
| FUZEON ® (Enfuvirtide or T-20) | Roche/Trimeris | HIV infection AIDs, viral Fusion inhibitor |
| LEXIVA ® (or Fosamprenavir calcium) | GSK/Vertex | HIV infection AIDs, viral protease inhibitor |
| SELZENTRY ® Maraviroc; (UK 427857) | Pfizer | HIV infection AIDs, (CCR5 antagonist, in development) |
| TRIZIVIR ® | GSK | HIV infection AIDs, (three drug combination) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| Integrase Inhibitor MK-0518 Raltegravir | Merck | HIV infection AIDs |
| TRUVADA ® | Gilead | Combination of Tenofovir disoproxil fumarate salt (VIREAD ®) and EMTRIVA ® (Emtricitabine) |
| Integrase Inhibitor GS917/JTK-303 Elvitegravir | Gilead/Japan Tobacco | HIV Infection AIDs in development |
| Triple drug combination ATRIPLA ® | Gilead/Bristol-Myers Squibb | Combination of Tenofovir disoproxil fumarate salt (VIREAD ®), EMTRIVA ® (Emtricitabine), and SUSTIVA ® (Efavirenz) |
| FESTINAVIR ® | Oncolys BioPharma | HIV infection AIDs in development |
| CMX-157 Lipid conjugate of nucleotide tenofovir | Chimerix | HIV infection AIDs |
| GSK1349572 Integrase inhibitor | GSK | HIV infection AIDs |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | Wyeth Lederle Labs | AIDS, Kaposi's sarcoma |
| FP-21399 | Fuki ImmunoPharm | Blocks HIV fusion with CD4 + cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |

-continued

| Drug Name | Manufacturer | Indication |
|---|---|---|
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the disclosure herein set forth may be used in combination with HIV entry inhibitors. Examples of such HIV entry inhibitors are discussed in DRUGS OF THE FUTURE 1999, 24(12), pp. 1355-1362; CELL, Vol. 9, pp. 243-246, Oct. 29, 1999; and DRUG DISCOVERY TODAY, Vol. 5, No. 5, May 2000, pp. 183-194 and *Inhibitors of the entry of HIV into host cells*. Meanwell, Nicholas A.; Kadow, John F. Current Opinion in Drug Discovery & Development (2003), 6(4), 451-461. Specifically the compounds can be utilized in combination with attachment inhibitors, fusion inhibitors, and chemokine receptor antagonists aimed at either the CCR5 or CXCR4 coreceptor. HIV attachment inhibitors are also set forth in U.S. Pat. No. 7,354,924 and US 2005/0209246.

It will be understood that the scope of combinations of the compounds of this application with AIDS antivirals, immunomodulators, anti-infectives, HIV entry inhibitors or vaccines is not limited to the list in the above Table but includes, in principle, any combination with any pharmaceutical composition useful for the treatment of AIDS.

Preferred combinations are simultaneous or alternating treatments with a compound of the present disclosure and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is REYATAZ® (active ingredient Atazanavir). Typically a dose of 300 to 600 mg is administered once a day. This may be co-administered with a low dose of Ritonavir (50 to 500 mgs). Another preferred inhibitor of HIV protease is KALETRA®. Another useful inhibitor of HIV protease is indinavir, which is the sulfate salt of N-(2 (R)-hydroxy-1-(S)-indanyl) -2(R)-phenylmethyl-4-(S)-hydroxy-5-(1-(4-(3-pyridyl-methyl)-2(S)-N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) tenofovir disoproxil fumarate salt and emtricitabine.

In such combinations the compound of the present invention and other active agents may be administered separately or in conjunction. In addition, the administration of one element may be prior to, concurrent to, or subsequent to the administration of other agent(s).

GENERAL CHEMISTRY (METHODS OF SYNTHESIS)

The present invention comprises compounds of Formula I, their pharmaceutical formulations, and their use in patients suffering from or susceptible to HIV infection. The compounds of Formula I also include pharmaceutically acceptable salts thereof. General procedures to construct compounds of Formula I and intermediates useful for their synthesis are described in the following Schemes (after the Abbreviations).

Abbreviations

One or more of the following abbreviations, most of which are conventional abbreviations well known to those skilled in the art, may be used throughout the description of the disclosure and the examples:

$Bz_2O$=benzoic anhydride
TBTU=O-(benzotriazol-1-yl)-N,N,N',N'-tetramethyluronium tetrafluoroborate
HATU=2-(1H-7-azabenzotriazol-1-yl)-1,1,3,3-tetramethyluronium hexafluorophosphate methanaminium
DCE=dichloroethane DCM=dichloromethane
CDI=carbonyl diimidazole
prep. HPLC=preparative high performance liquid chromatography
rt=room temperature
DIPEA=diisopropylethylamine
DMAP=4-dimethylaminopyridine
DMSO=dimethylsulfoxide
THF=tetrahydrofuran
KHMDS=potassium bis(trimethylsilyl)amide
min=minute(s)
h=hour(s)
sat.=saturated
TEA=triethylamine
EtOAc=ethyl acetate
TFA=trifluoroacetic acid
PCC=pyridinium chlorochromate
TLC=thin layer chromatography
Tf$_2$NPh=(trifluoromethylsulfonyl)methanesulfonamide
dioxane=1,4-dioxane
PG=protective group
atm=atmosphere(s)
mol=mole(s)
mmol=milimole(s)
mg=milligram(s)
μg=microgram(s)
μl=microliter(s)
μm=micrometer(s)
mm=millimeter(s)
HOAc=acetic acid
MeOH=methanol
DMF=N,N-dimethylformamide
TBAF=tetrabutylammonium fluoride
Preparation of Compounds of Formula I General Chemistry Schemes:

Compounds of Formula I can be prepared from commercially available (Aldrich, others) betulinic acid by chemistry described in the following schemes.

General Reaction Schemes are Set Forth as Follows:

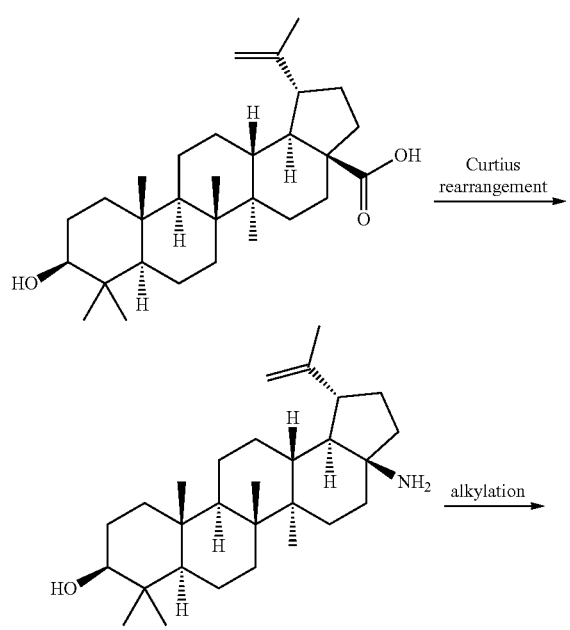

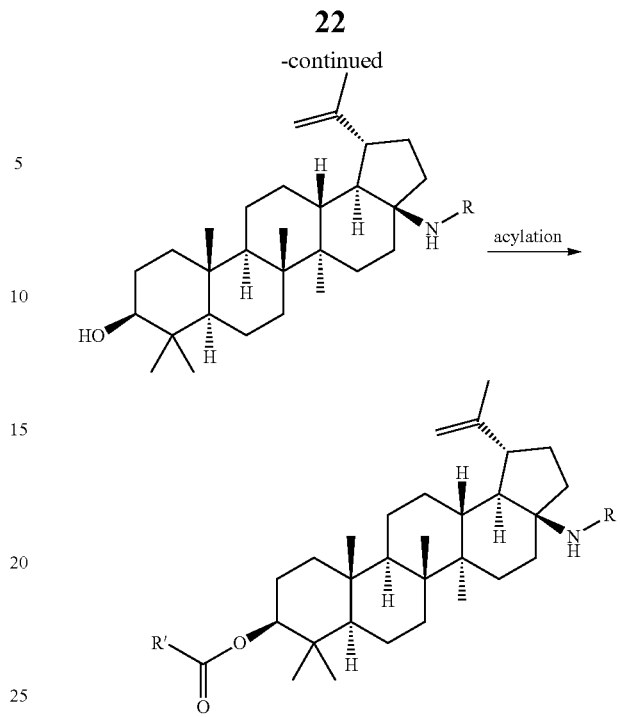

Betulinic acid can be converted into the corresponding C-17 amine analog via Curtius' rearrangement. Selective alkylation of the amine can be achieved by treatment with an alkylating agent (R-LG), where LG is a leaving group such as, but not limited to Br, C, I, mesylate, tosylate or triflate in the presence of a base. Heating maybe needed in some cases. In some cases, by prolonging the reaction times and heating the reaction mixture, the dialkylated product can also be formed. Acylation of the C-3 hydroxyl can be achieved by heating in the presence of the corresponding anhydride. Alternatively, acylation can also be accomplished by addition of the corresponding carboxylic acid and a couping agent such as, but not limited to HATU or TBTU. Saturation of the double bond can be performed under standard conditions in any stage of the synthesis.

EXAMPLES

The following examples illustrate typical syntheses of the compounds of Formula I as described generally above. These examples are illustrative only and are not intended to limit the disclosure in any way. The reagents and starting materials are readily available to one of ordinary skill in the art.

Chemistry

Typical Procedures and Characterization of Selected Examples:

Unless otherwise stated, solvents and reagents were used directly as obtained from commercial sources, and reactions were performed under a nitrogen atmosphere. Flash chromatography was conducted on Silica gel 60 (0.040-0.063 particle size; EM Science supply). $^1$H NMR spectra were recorded on Bruker DRX-500f at 500 MHz (or Bruker AV 400 MHz, Bruker DPX-300B or Varian Gemini 300 at 300 MHz as stated). The chemical shifts were reported in ppm on the δ scale relative to δTMS=0. The following internal references were used for the residual protons in the following solvents: CDCl$_3$ ($\delta_H$ 7.26), CD$_3$OD ($\delta_H$ 3.30), Acetic-d4 (Acetic Acid d$_4$) ($\delta_H$ 11.6, 2.07), DMSO mix or DMSO-D6_CDCl$_3$ (($_H$ 2.50 and 8.25) (ratio 75%:25%), and DMSO-D6 ($\delta_H$ 2.50). Standard acronyms were employed to describe the multiplicity patterns: s (singlet), br. s (broad singlet), d (doublet), t (triplet), q (quartet), m (multiplet), b (broad), app (apparent). The coupling constant (J) is in Hertz. All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.
LC/MS Methods:
Method 1
Start % B=0, final % B=100 over 2 minute gradient
Flow rate=1 mL/min
Solvent A=95% H$_2$O/5% MeOH/10 mM NH$_4$OAc
Solvent B=5% H$_2$O/95% MeOH/10 mM NH$_4$OAc
Column=PHENOMENEX-LUNA 2.0×30 mm 3 μm Preparation of Compounds Example 1 and Example 2

Preparation of 4-(((1R,3aS,5aR,5bR,7aR,9S,11aR, 13aR,13bR)-3a-((2-(1,1-dioxido-4-thiomorpholinyl) ethyl)amino)-1-isopropenyl-5a,5b,8,8,11a-pentam-ethylicosahydro-1H-cyclopenta[a]chrysen-9-yl)oxy)-3,3-dimethyl-4-oxobutanoic acid and 4-(((1R,3aS, 5aR,5bR,7aR,9S,11aR,13aR,13bR)-3a-((2-(1,1-dioxido-4-thiomorpholinyl)ethyl)amino)-1-isopropenyl-5a,5b,8,8,11a-pentamethylicosahydro-1H-cyclopenta[a]chrysen-9-yl)oxy)-2,2-dimethyl-4-oxobutanoic acid

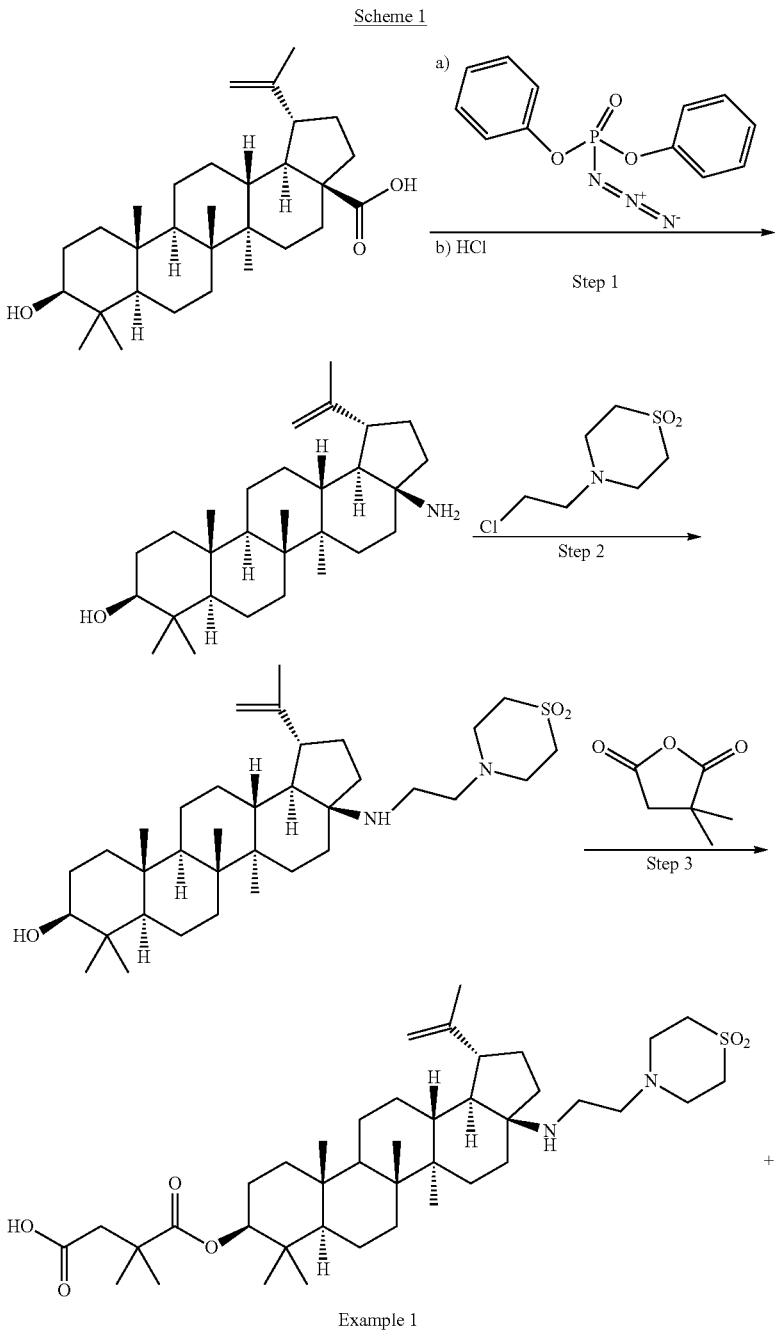

Scheme 1

Example 1

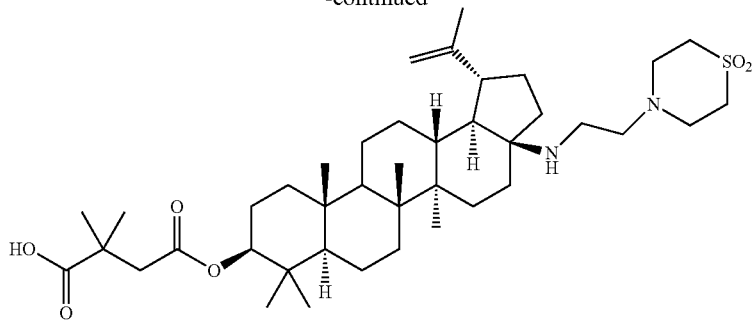

Example 2

Step 1: Preparation of (1R,3aS,5aR,5bR,7aR,9S, 11aR,11bR,13aR,13bR)-3a-amino-5a,5b,8,8,11a-pentamethyl-1-(prop-1-en-2-yl)icosahydro-1H-cyclopenta[a]chrysen-9-ol

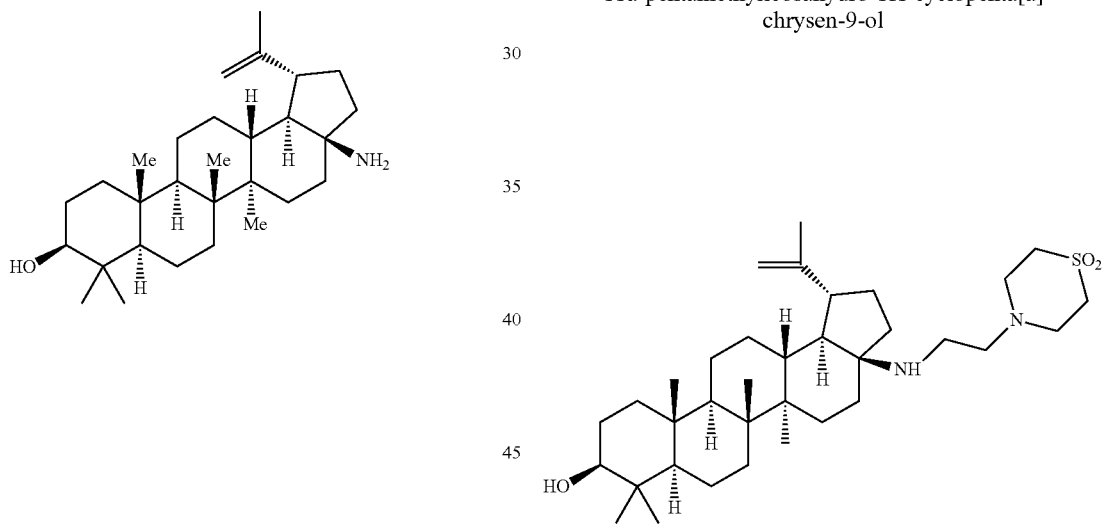

a) A mixture of (1R,3aS,5aR,5bR,7aR,9S,11aR,11bR,13aR, 13bR)-9-hydroxy-5a,5b,8,8,11a-pentamethyl-1-(prop-1-en-2-yl)icosahydro-1H-cyclopenta[a]chrysene-3a-carboxylic acid (5 g, 10.95 mmol), diphenyl phosphorazidate (3.54 mL, 16.42 mmol) and triethylamine (4.58 mL, 32.8 mmol) in toluene (50 mL) was refluxed for 16 h at 110° C. The reaction mixture was concentrated under reduced pressure and the residue was purified in silica gel using 6-30% ethyl acetate/hexanes to provide the title compound as white solid (2.8 g).

b) To this intermediate (2.8 g, 6.17 mmol) in THF (20 mL) was added HCl (4N, 10.14 mL, 123 mmol) and the reaction mixture was heated up at 60° C. for 48 h. The reaction mixture was concentrated under reduced pressure and the residue was purified in silica gel using 0-10% methylene chloride/methanol/5% TEA. The resulting solid was recrystallized in methanol/dioxane/water to provide the title compound as a white solid (2.3 g, 50%). LCMS: m/e 428.23 (M+H)$^+$, 2.26 min (method 1). $^1$H NMR (500 MHz, Acetic) δ 4.86 (s, 1H), 4.73 (s, 1H), 3.32 (dd, J=10.4, 5.5 Hz, 1H), 2.78 (d, J=6.1 Hz, 1H), 2.38-2.12 (m, 2H), 1.98-0.93 (m, 22H), 1.76 (s, 3H), 1.13 (s, 3H), 1.07 (s, 3H), 0.99 (s, 3H), 0.90 (s, 3H), 0.81 (s, 3H).

Step 2: Preparation of (1R,3aS,5aR,5bR,7aR,9S, 11aR,11bR,13aR,13bR)-3a-((2-(1,1-dioxido-4-thiomorpholinyl)ethyl)amino)-1-isopropenyl-5a,5b,8,8, 11a-pentamethylicosahydro-1H-cyclopenta[a]chrysen-9-ol A mixture of (1R,3aS,5aR,5bR,7aR,9S,11aR,11bR,13aR, 13bR)-3a-amino-5a,5b,8,8,11a-pentamethyl-1-(prop-1-en-2-yl)icosahydro-1H-cyclopenta[a]chrysen-9-ol (1.03 g, 2.408 mmol), 4-(2-chloroethyl)thiomorpholine (1.428 g, 7.22 mmol), potassium phosphate (2.045 g, 9.63 mmol) and potassium iodide (0.959 g, 5.78 mmol) in acetonitrile (5 mL) was heated up at 120° C. for 20 h. The reaction mixture was concentrated under reduced pressure and the crude was purified in silica gel using 10-100% ethyl acetate/hexanes to provide the title compound as a white solid (0.9 g, 64%). LCMS: m/e 589.38 (M+H)$^+$, 2.46 min (method 1).

Step 3: Preparation of 4-(((1R,3aS,5aR,5bR,7aR,9S,11aR,13aR,13bR)-3a-((2-(1,1-dioxido-4-thiomorpholinyl)ethyl)amino)-1-isopropenyl-5a,5b,8,8,11a-pentamethylicosahydro-1H-cyclopenta[a]chrysen-9-yl)oxy)-3,3-dimethyl-4-oxobutanoic acid

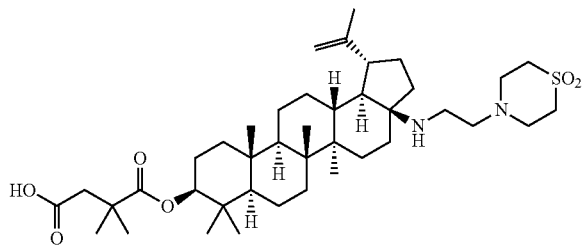

Example 1 and 4-(((1R,3aS,5aR,5bR,7aR,9S,11aR,13aR,13bR)-3a-((2-(1,1-dioxido-4-thiomorpholinyl)ethyl)amino)-1-isopropenyl-5a,5b,8,8,11a-pentamethylicosahydro-1H-cyclopenta[a]chrysen-9-yl)oxy)-2,2-dimethyl-4-oxobutanoic acid

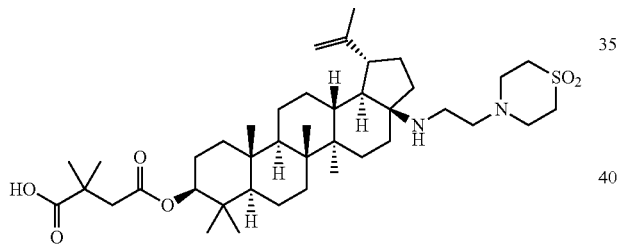

Example 2

A mixture of (1R,3aS,5aR,5bR,7aR,9S,11aR,11bR,13aR,13bR)-3a-((2-(1,1-dioxido-4-thiomorpholinyl)ethyl)amino)-1-isopropenyl-5a,5b,8,8,11a-pentamethylicosahydro-1H-cyclopenta[a]chrysen-9-ol (100 mg, 0.170 mmol), 3,3-dimethyldihydrofuran-2,5-dione (436 mg, 3.4 mmol) and DMAP (208 mg, 1.7 mmol) in pyridine (1 mL) was heated up at 150° C. for 37 h. The reaction mixture was filtered and purified by prep. HPLC to provide the title compounds 4-(((1R,3aS,5aR,5bR,7aR,9S,11aR,13aR,13bR)-3a-((2-(1,1-dioxido-4-thiomorpholinyl)ethyl)amino)-1-isopropenyl-5a,5b,8,8,11a-pentamethylicosahydro-1H-cyclopenta[a]chrysen-9-yl)oxy)-3,3-dimethyl-4-oxobutanoic acid, example 1, as a white solid (17 mg, 13%). LCMS: m/e 717.51 (M+H)$^+$, 2.39 min (method 1). $^1$H NMR (500 MHz, Acetic) δ 4.83 (s, 1H), 4.75 (s, 1H), 4.51 (dd, J=10.8, 5.6 Hz, 1H), 3.41-3.11 (m, 11H), 3.10-2.99 (m, 1H), 2.82 (td, J=10.8, 5.5 Hz, 1H), 2.75-2.63 (m, 2H), 2.27-1.04 (m, 24H), 1.76 (s, 3H), 1.31 (s, 6H), 1.19 (s, 3H), 1.13 (s, 3H), 0.95 (s, 3H), 0.92 (s, 3H), 0.92 (s, 3H) and 4-(((1R,3aS,5aR,5bR,7aR,9S,11aR,13aR,13bR)-3a-((2-(1,1-dioxido-4-thiomorpholinyl)ethyl)amino)-1-isopropenyl-5a,5b,8,8,11a-pentamethylicosahydro-1H-cyclopenta[a]chrysen-9-yl)oxy)-2,2-dimethyl-4-oxobutanoic acid, example 2, as a white solid (60 mg, 47%). LCMS: m/e 717.51 (M+H)$^+$, 2.44 min (method 1). $^1$H NMR (500 MHz, Acetic) δ 4.82 (s, 1H), 4.72 (s, 1H), 4.57 (dd, J=10.2, 6.0 Hz, 1H), 3.44 (d, J=12.5 Hz, 1H), 3.35-3.20 (m, 6H), 3.19-3.09 (m, 3H), 3.05 (d, J=4.6 Hz, 2H), 2.97-2.85 (m, 1H), 2.81-2.58 (m, 2H), 2.32-2.13 (m, 2H), 1.79-1.05 (m, 22H), 1.75 (s, 3H), 1.33 (s, 3H), 1.31 (s, 3H), 1.23 (s, 3H), 1.11 (s, 3H), 0.96 (s, 3H), 0.90 (s, 3H), 0.89 (s, 3H).

Example 3

Preparation of 5-(((1R,3aS,5aR,5bR,7aR,9aR,9S,11aR,3aR,13bR)-3a-((2-(1,1-dioxido-4-thiomorpholinyl)ethyl)amino)-1-isopropenyl-5a,5b,8,8,11a-pentamethylicosahydro-1H-cyclopenta[a]chrysen-9-yl)oxy)-3,3-dimethyl-5-oxopentanoic acid

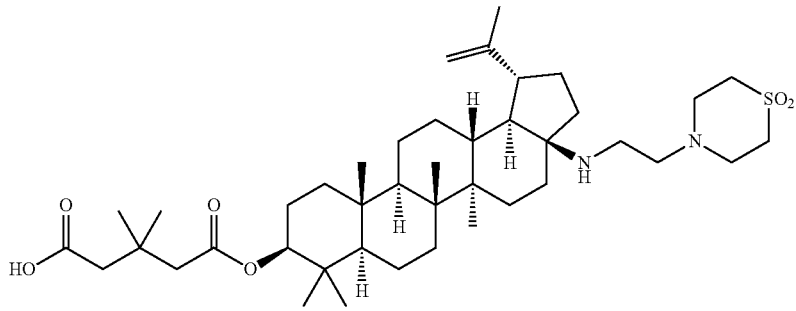

A mixture of (1R,3aS,5aR,5bR,7aR,9S,11aR,11bR,13aR,13bR)-3a-((2-(1,1-dioxido-4-thiomorpholinyl)ethyl)amino)-1-isopropenyl-5a,5b,8,8,11a-pentamethylicosahydro-1H-cyclopenta[a]chrysen-9-ol (50 mg, 0.085 mmol), 4,4-dimethyldihydro-2H-pyran-2,6(3H)-dione (242 mg, 1.7 mmol) and DMAP (104 mg, 0.85 mmol) in pyridine (1 mL) was heated up at 150° C. for 33 h. The reaction mixture was filtered to remove any solids and the clear solution was purified by prep. HPLC to provide the title compound as a white solid (48 mg, 74%). LCMS: m/e 731.48 (M+H)$^+$, 2.44 min (method 1). $^1$H NMR (500 MHz, Acetic) δ 4.82 (s, 1H), 4.73 (s, 1H), 4.63-4.50 (m, 1H), 3.44 (d, J=12.5 Hz, 1H), 3.36-3.20 (m, 6H), 3.19-3.11 (m, 3H), 3.09-3.01 (m, 2H), 2.99-2.85 (m, 1H), 2.66-2.42 (m, 4H), 2.31-1.06 (m, 24H), 1.75 (s, 3H), 1.23 (s, 3H), 1.18 (s, 3H), 1.17 (s, 3H), 1.12 (s, 3H), 0.98 (s, 3H), 0.93 (s, 6H).

Example 4 and Example 5

Preparation of 3,3-dimethyl-4-oxo-4-((1R,3aS,5aR, 5bR,7aR,9S,11aR,13aR,13bR)-5a,5b,8,8,11a-pentamethyl-3a-(2-morpholinoethylamino)-1-(prop-1-en-2-yl)icosahydro-1H-cyclopenta[a]chrysen-9-yloxy)butanoic acid and 2,2-dimethyl-4-oxo-4-((1R, 3aS,5aR,5bR,7aR,9S,11aR,13aR,13bR)-5a,5b,8,8, 11a-pentamethyl-3a-(2-morpholinoethylamino)-1-(prop-1-en-2-yl)icosahydro-1H-cyclopenta[a]chrysen-9-yloxy)butanoic acid The title compounds were prepared following the method described in scheme 1 using 4-(2-chloroethyl)morpholine as alkylating reagent instead of 4-(2-chloroethyl)thiomorpholine. The crude material was purified using reverse phase prep HPLC to afford 3,3-dimethyl-4-oxo-4-((1R,3aS,5aR,5bR, 7aR,9S,1aR,13aR,13bR)-5a,5b,8,8,11a-pentamethyl-3a-(2-morpholinoethylamino)-1-(prop-1-en-2-yl)icosahydro-1H-cyclopenta[a]chrysen-9-yloxy)butanoic acid, example 4, as a white solid (4 mg, 8%). LCMS: m/e 669.36 (M+H)$^+$, 2.51 min (method 1). $^1$H NMR (500 MHz, Acetic) δ 4.85 (s, 1H), 4.73 (s, 1H), 4.54 (dd, J=10.8, 5.6 Hz, 1H), 3.94 (br. s., 4H), 3.73-3.51 (m, 4H), 3.29 (br. s., 4H), 2.91-2.79 (m, 1H), 2.75-2.65 (m, 2H), 2.26-1.03 (m, 24H), 1.76 (s, 3H), 1.32 (s, 6H), 1.16 (s, 3H), 1.10 (s, 3H), 0.95 (s, 3H), 0.93 (s, 3H), 0.92 (s, 3H) and 2,2-dimethyl-4-oxo-4-((1R,3aS,5aR,5bR,7aR,9S, 11aR,13aR,13bR)-5a,5b,8,8,11a-pentamethyl-3a-(2-morpholinoethylamino)-1-(prop-1-en-2-yl)icosahydro-1H-cyclopenta[a]chrysen-9-yloxy)butanoic acid, example 5, as a white solid (23 mg, 44%). LCMS: m/e 669.55 (M+H)$^+$, 2.58 min (method 1). $^1$H NMR (500 MHz, Acetic) δ 4.84 (s, 1H), 4.73 (s, 1H), 4.61-4.52 (m, 1H), 3.94 (br. s., 4H), 3.72-3.52 (m, 4H), 3.28 (br. s., 4H), 2.89-2.79 (m, 1H), 2.78-2.62 (m,

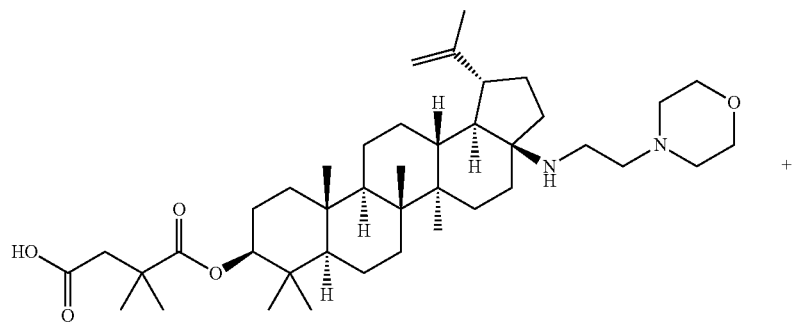

example 4

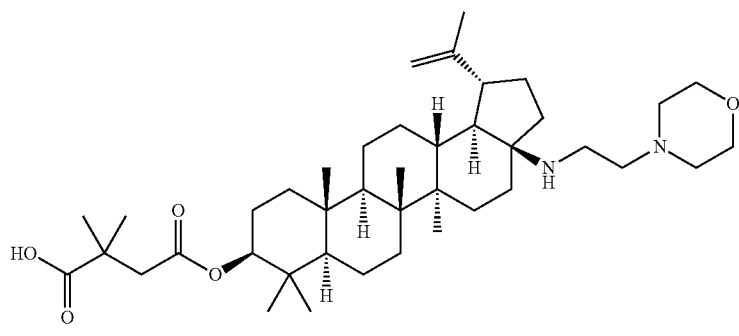

example 5

2H), 2.28-1.19 (m, 24H), 1.75 (s, 3H), 1.33 (s, 3H), 1.31 (s, 3H), 1.15 (s, 3H), 1.10 (s, 3H), 0.94 (s, 3H), 0.90 (s, 3H), 0.88 (s, 3H).

Example 6

Preparation of 4-(((1S,3aS,5aR,5bR,7aR,9S,11aR, 13aR,13bR)-3a-((2-(1,1-dioxido-4-thiomorpholinyl) ethyl)amino)-1-isopropyl-5a,5b,8,8,11a-pentamethylicosahydro-1H-cyclopenta[a]chrysen-9-yl)oxy)-2, 2-dimethyl-4-oxobutanoic acid

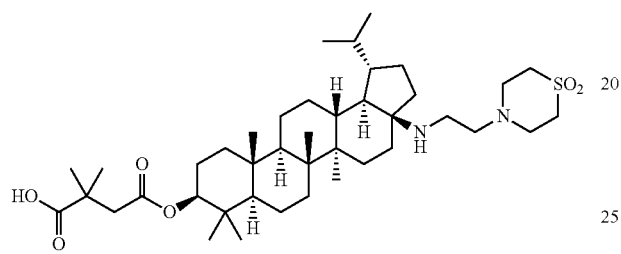

A mixture of 4-(((1R,3aS,5aR,5bR,7aR,9S,11aR,13aR, 13bR)-3a-((2-(1,1-dioxido-4-thiomorpholinyl)ethyl) amino)-1-isopropenyl-5a,5b,8,8,11a-pentamethylicosahydro-1H-cyclopenta[a]chrysen-9-yl)oxy)-2,2-dimethyl-4-oxobutanoic acid (10 mg, 0.014 mmol) and 10% palladium on carbon (14.84 mg, 0.014 mmol) in methanol (5 mL) was stirred at 20° C. for 18 h under hydrogen at 40 psi. The reaction mixture was filtered to remove the catalyst and the solution was purified by reverse phase prep HPLC to provide the title compound as a white solid (4.1 mg, 39%). LCMS: m/e 719.53 (M+H)$^+$, 2.41 min (method 1). $^1$H NMR (500 MHz, Acetic) δ 4.58 (dd, J=10.5, 5.6 Hz, 1H), 3.43-3.36 (m, 1H), 3.34-3.19 (m, 6H), 3.18-3.01 (m, 5H), 2.80-2.61 (m, 2H), 2.27-0.89 (m, 26H), 1.33 (s, 3H), 1.32 (s, 3H), 1.23 (s, 3H), 1.09 (s, 3H), 0.98 (s, 3H), 0.93 (d, J=6.7 Hz, 3H), 0.90 (s, 6H), 0.84 (d, J=6.7 Hz, 3H).

Example 7

Preparation of 5-(((1S,3aS,5aR,5bR,7aR,9aR,9S, 11aR,3aR,13bR)-3a-((2-(1,1-dioxido-4-thiomorpholinyl)ethyl)amino)-1-isopropyl-5a,5b,8,8,11a-pentamethylicosahydro-1H-cyclopenta[a]chrysen-9-yl)oxy)-3,3-dimethyl-5-oxopentanoic acid

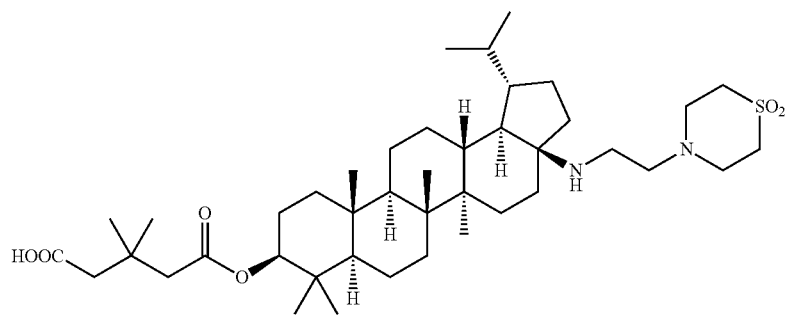

A mixture of 5-(((1R,3aS,5aR,5bR,7aR,9S,11aR,13aR,13bR)-3a-((2-(1,1-dioxido-4-thiomorpholinyl)ethyl)amino)-1-isopropenyl-5a,5b,8,8,11a-pentamethylicosahydro-1H-cyclopenta[a]chrysen-9-yl)oxy)-3,3-dimethyl-5-oxopentanoic acid (15 mg, 0.021 mmol) and 10% palladium on carbon (21.83 mg, 0.021 mmol) in methanol (5 mL) was stirred at 20° C. for 18 h under hydrogen at 35 psi. The reaction mixture was filtered to remove the catalyst and the solution was purified using reverse phase prep HPLC to provide the title compound as colorless oil (7 mg, 44%). LCMS: m/e 733.30 (M+H)$^+$, 2.44 min (method 1). $^1$H NMR (500 MHz, Acetic) δ 4.66-4.46 (m, 1H), 3.38 (d, J=11.6 Hz, 1H), 3.34-2.99 (m, 11H), 2.61-2.44 (m, 4H), 2.26-1.03 (m, 26H), 1.24 (s, 3H), 1.19 (s, 3H), 1.18 (s, 3H), 1.10 (s, 3H), 0.99 (s, 3H), 0.93 (s, 6H), 0.92 (d, J=6.7 Hz, 3H), 0.85 (d, J=6.7 Hz, 3H).

Example 8 and Example 9

Preparation of 3,3-dimethyl-4-oxo-4-(((1R,3aS,5aR,5bR,7aR,9S,11aR,13aR,13bR)-5a,5b,8,8,11a-pentamethyl-3a-((2-(4-(methylsulfonyl)piperidin-1-yl)ethyl)amino)-1-(prop-1-en-2-yl)icosahydro-1H-cyclopenta[a]chrysen-9-yl)oxy)butanoic acid and 2,2-dimethyl-4-oxo-4-(((1R,3aS,5aR,5bR,7aR,9S,11aR,13aR,13bR)-5a,5b,8,8,11a-pentamethyl-3a-((2-(4-(methylsulfonyl)piperidin-1-yl)ethyl)amino)-1-(prop-1-en-2-yl)icosahydro-1H-cyclopenta[a]chrysen-9-yl)oxy)butanoic acid The title compounds were prepared following the method described in scheme 1 using 1-(2-chloroethyl)-4-(methylsulfonyl)piperidine as alkylating reagent instead of 4-(2-chloroethyl)thiomorpholine. 3,3-dimethyl-4-oxo-4-(((1R,3aS,5aR,5bR,7aR,9S,11aR,13aR,13bR)-5a,5b,8,8,11a-pentamethyl-3a-((2-(4-(methylsulfonyl)piperidin-1-yl)ethyl)amino)-1-(prop-1-en-2-yl)icosahydro-1H-cyclopenta[a]chrysen-9-yl)oxy)butanoic acid, example 8, was isolated as a white solid (1.5 mg, 7%). LCMS: m/e 745.6 (M+H)$^+$, 2.3 min (method 1). $^1$H NMR (500 MHz, Acetic) δ 4.85 (s, 1H), 4.74 (s, 1H), 4.54 (dd, J=10.8, 5.0 Hz, 1H), 3.80-3.50 (m, 6H), 3.46-3.26 (m, 1H), 3.09-3.02 (m, 2H), 3.02 (s, 3H), 2.90-2.74 (m, 1H), 2.76-2.61 (m, 2H), 2.47-2.32 (m, 2H), 2.26-1.05 (m, 26H), 1.76 (s, 3H), 1.32 (s, 6H), 1.16 (s, 3H), 1.10 (s, 3H), 0.95 (s, 3H), 0.93 (s, 3H), 0.92 (s, 3H). 2,2-dimethyl-4-oxo-4-(((1R,3aS,5aR,5bR,7aR,9S,11aR,13aR,13bR)-5a,5b,8,8,11a-pentamethyl-3a-((2-(4-(methylsulfonyl)piperidin-1-yl)ethyl)amino)-1-(prop-1-en-2-yl)icosahydro-1H-cyclopenta[a]chrysen-9-yl)oxy)butanoic acid, example 9, was isolated as a white solid (8.2 mg, 36%). LCMS: m/e 743.55 (M−H)$^-$, 2.34 min (method 1). $^1$H NMR (400 MHz, Acetic) δ 4.81 (s, 1H), 4.69 (s, 1H), 4.60-4.45 (m, 1H), 3.77-3.43 (m, 6H), 3.38-3.22 (m, 1H), 3.06-2.92 (m, 2H), 2.97 (s, 3H), 2.82-2.73 (m, 1H), 2.73-2.59 (m, 2H), 2.44-2.27 (m, 2H), 2.19-1.01 (m, 26H), 1.72 (s, 3H), 1.29 (s, 3H), 1.27 (s, 3H), 1.12 (s, 3H), 1.06 (s, 3H), 0.90 (s, 3H), 0.86 (s, 3H), 0.85 (s, 3H).

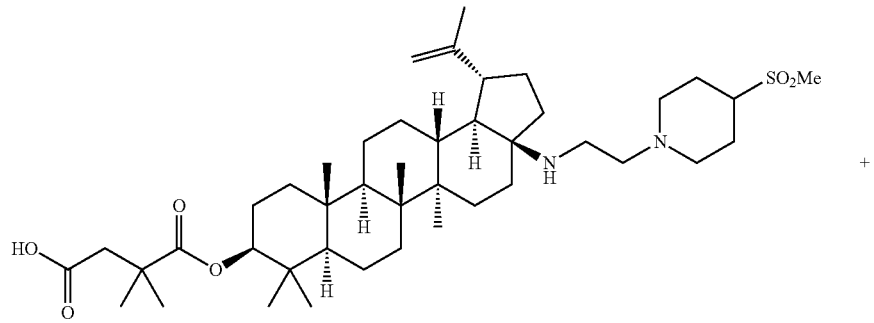

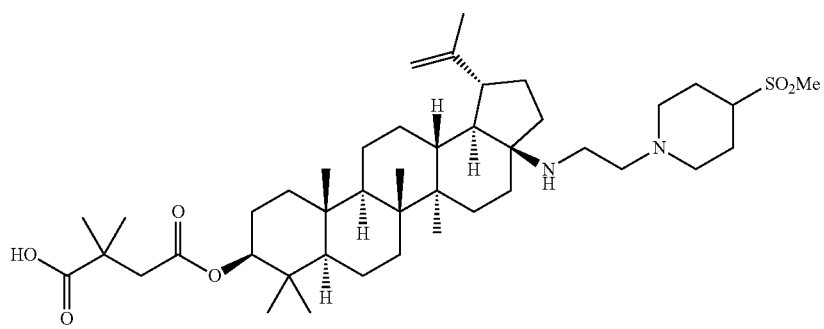

Example 10

Preparation of 4-(((1R,3aS,5aR,5bR,7aR,9S,11aR,13aR,13bR)-3a-((2-(dimethylamino)ethyl)amino)-5a,5b,8,8,11a-pentamethyl-1-(prop-1-en-2-yl)icosahydro-1H-cyclopenta[a]chrysen-9-yl)oxy)-2,2-dimethyl-4-oxobutanoic acid

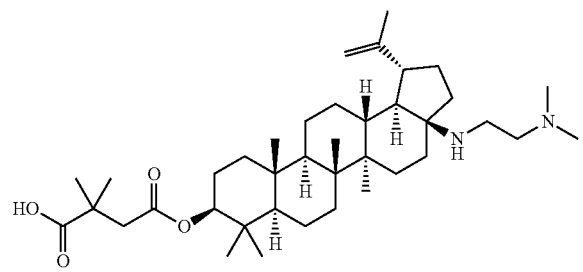

The title compound was prepared following the method described in scheme 1 using 2-chloro-N,N-dimethylethanamine hydrochloride as alkylating reagent instead of 4-(2-chloroethyl)thiomorpholine. The product was isolated as a white solid (0.6 mg, 23%). LCMS: m/e 627.6 (M+H)$^+$, 2.39 min (method 1). $^1$H NMR (500 MHz, Acetic) δ 4.85 (s, 1H), 4.74 (s, 1H), 4.63-4.47 (m, 1H), 3.94-3.59 (m, 4H), 3.00 (s, 6H), 2.88-2.77 (m, 1H), 2.77-2.59 (m, 2H), 2.39-1.18 (m, 24H), 1.76 (s, 3H), 1.32 (s, 3H), 1.31 (s, 3H), 1.12 (s, 3H), 1.10 (s, 3H), 0.93 (s, 3H), 0.89 (s, 3H), 0.88 (s, 3H).

Preparation of 2,2-dimethyl-4-oxo-4-(((1R,3aS,5aR,5bR,7aR,9S,11aR,11bR,13aR,13bR)-5a,5b,8,8,11a-pentamethyl-3a-((2-(4-(methylsulfonyl)piperazin-1-yl)ethyl)amino)-1-(prop-1-en-2-yl)icosahydro-1H-cyclopenta[a]chrysen-9-yl)oxy)butanoic acid

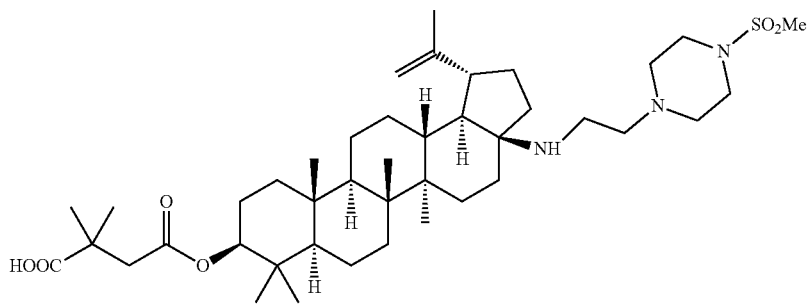

The title compound was prepared following the method described in scheme 1 using 1-(2-chloroethyl)-4-(methylsulfonyl)piperazine as alkylating reagent instead of 4-(2-chloroethyl)thiomorpholine. The product was isolated as a white solid (5.1 mg, 40%). LCMS: m/e 746.6 (M+H)$^+$, 2.15 min (method 1). $^1$H NMR (500 MHz, Acetic) δ 4.84 (s, 1H), 4.73 (s, 1H), 4.62-4.47 (m, 1H), 3.70-3.37 (m, 7H), 3.31 (dd, J=12.2, 6.1 Hz, 1H), 3.16 (br. s., 4H), 2.93 (s, 3H), 2.90-2.82 (m, 1H), 2.79-2.62 (m, 2H), 2.29-1.00 (m, 24H), 1.75 (s, 3H), 1.33 (s, 3H), 1.31 (s, 3H), 1.19 (s, 3H), 1.10 (s, 3H), 0.94 (s, 3H), 0.89 (s, 3H), 0.88 (s, 3H).

Biology Data for the Examples

"μM" means micromolar;
"mL" means milliliter;
"μl" means microliter;
"mg" means milligram;
"μg" means microgram;

The materials and experimental procedures used to obtain the results reported in Tables 1-2 are described below.

HIV Cell Culture Assay—MT-2 cells and 293T cells were obtained from the NIH AIDS Research and Reference Reagent Program. MT-2 cells were propagated in RPMI 1640 media supplemented with 10% heat inactivated fetal bovine serum, 100 μg/ml penicillin G and up to 100 units/ml streptomycin. The 293T cells were propagated in DMEM media supplemented with 10% heat inactivated fetal bovine serum (FBS), 100 units/ml penicillin G and 100 μg/ml streptomycin. The proviral DNA clone of $NL_{4-3}$ was obtained from the NIH AIDS Research and Reference Reagent Program. A recombinant $NL_{4-3}$ virus, in which a section of the nef gene from NL4-3 was replaced with the *Renilla* luciferase gene, was used as a reference virus. In addition, residue Gag P373 was converted to P373S. Briefly, the recombinant virus was prepared by transfection of the altered proviral clone of $NL_{4-3}$. Transfections were performed in 293T cells using LipofectAMINE PLUS from Invitrogen (Carlsbad, Calif.), according to manufacturer's instruction. The virus was titered in MT-2 cells using luciferase enzyme activity as a marker. Luciferase was quantitated using the Dual Luciferase kit from Promega (Madison, Wis.), with modifications to the manufacturer's protocol. The diluted Passive Lysis solution was pre-mixed with the re-suspended Luciferase Assay Reagent and the re-suspended Stop & Glo Substrate (2:1:1 ratio). Fifty (50) μL of the mixture was added to each aspirated well on assay plates and luciferase activity was measured immediately on a Wallac TriLux (Perkin-Elmer). Antiviral activities of inhibitors toward the recombinant virus were quantified by measuring luciferase activity in cells infected for 4-days with NLRluc recombinants in the presence serial dilutions of the inhibitor. The $EC_{50}$ data for the compounds is shown in Table 2. Table 1 is the key for the data in Table 2.

Results

TABLE 1

Biological Data Key for $EC_{50}$

| Compounds with $EC_{50}$ >0.1 μM | Compounds with $EC_{50}$ <0.1 μM |
|---|---|
| Group "B" | Group "A" |

TABLE 2

| Example # | Structure | 10% FBS (EC$_{50}$, uM) |
|---|---|---|
| 1 | 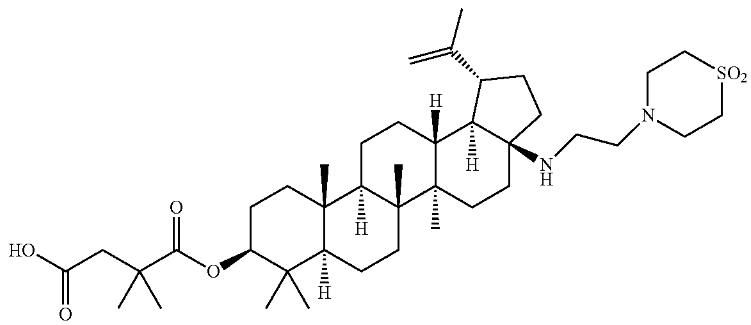 | A |
| 2 | 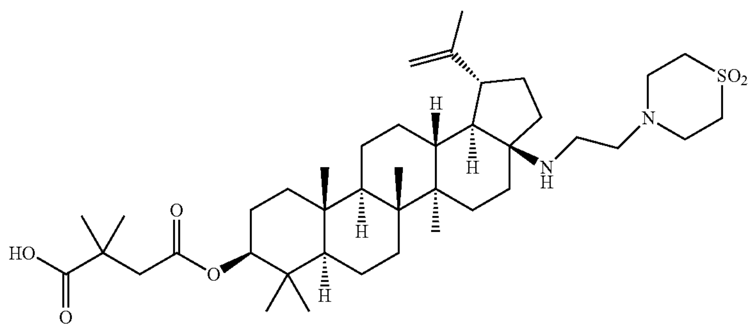 | A |
| 3 | 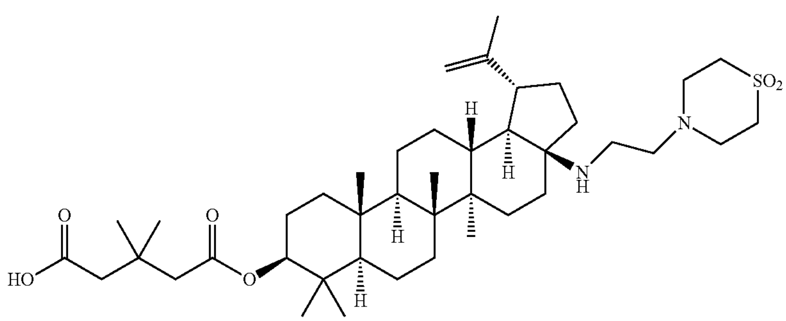 | A |
| 4 | 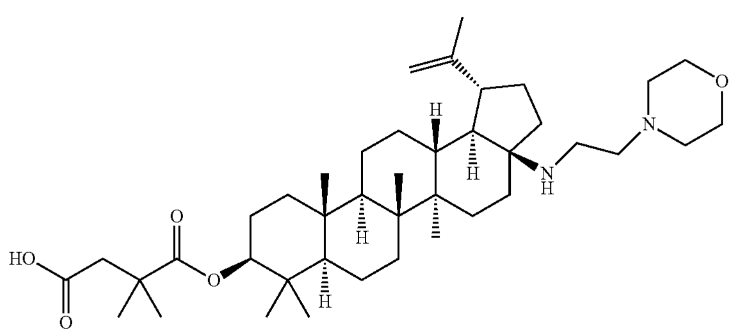 | A |

TABLE 2-continued

| Example # | Structure | 10% FBS (EC$_{50}$, uM) |
|---|---|---|
| 5 | 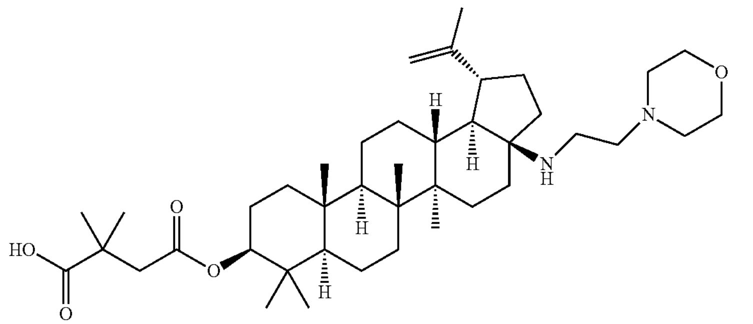 | A |
| 6 | 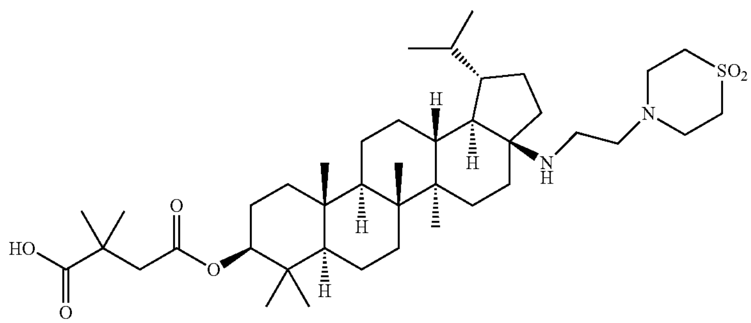 | A |
| 7 | 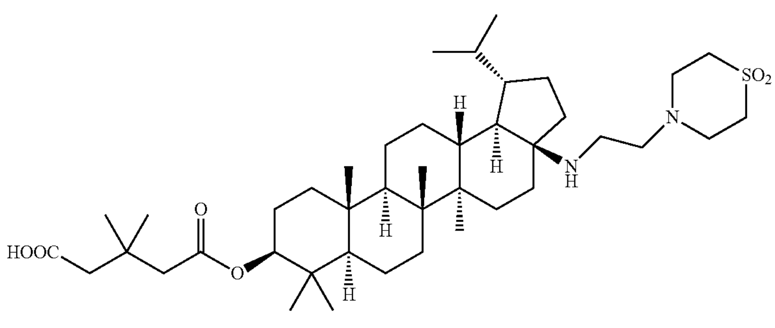 | A |
| 8 | 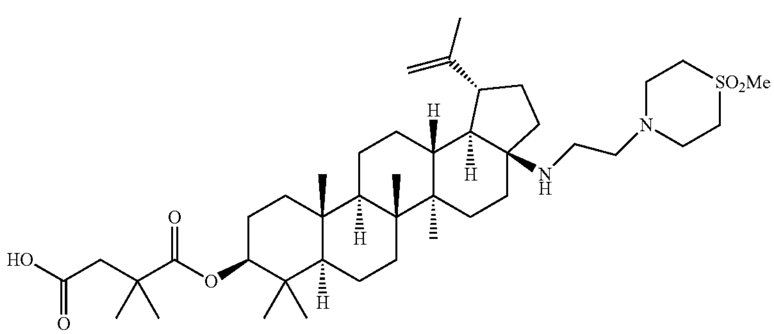 | A |

TABLE 2-continued

| Example # | Structure | 10% FBS (EC$_{50}$, uM) |
|---|---|---|
| 9 | 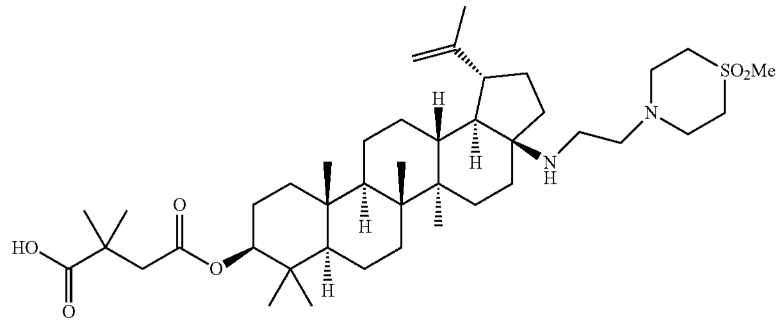 | A |
| 10 | 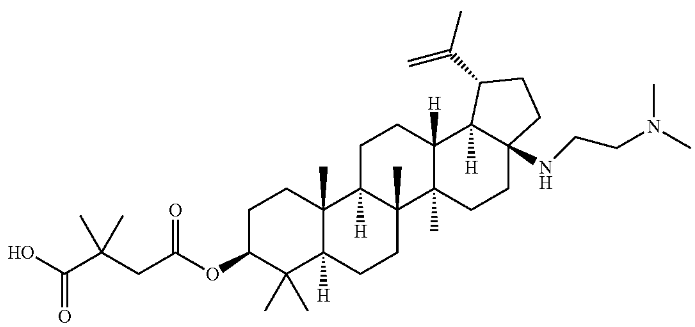 | A |
| 11 | 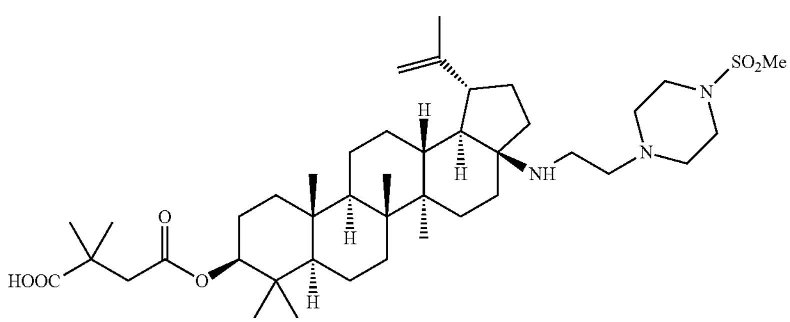 | A |

The foregoing description is merely illustrative and should not be understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

What is claimed is:

1. A compound of Formula I, including pharmaceutically acceptable salts thereof:

Formula I

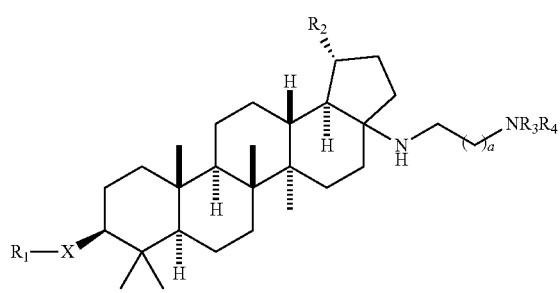

wherein a is 1 to 4;

X is —O;

R$_1$ is —C(O)CH$_2$C(CH$_3$)$_2$COOH, —C(O)C(CH$_3$)$_2$CH$_2$COOH, or —C(O)CH$_2$C(CH$_3$)$_2$CH$_2$COOH;

R$_2$ is selected from the group of —H, methyl, isopropenyl and isopropyl;

R$_3$ and R$_4$ are independently selected from the group of —H, —C$_{1-6}$ alkyl, —C$_{1-6}$ alkylsubstituted alkyl and —C$_{3-6}$ cycloalkyl;

or R$_3$ and R$_4$ are taken together with the adjacent N to form a cycle selected from the group of:

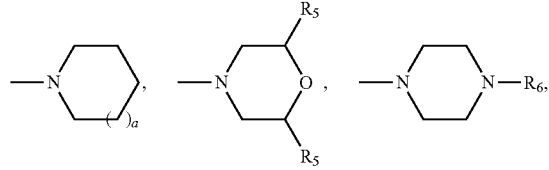

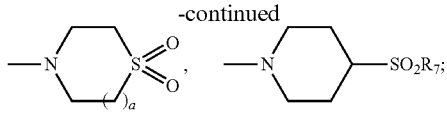

R$_5$ is independently —H or —C$_{1-6}$ alkyl;

R$_6$ is selected from the group of —SO$_2$R$_7$, —SO$_2$NR$_8$R$_9$

R$_7$ is selected from the group of —C$_{1-6}$ alkyl, —C$_{1-6}$ alkyl-substituted alkyl, —C$_{3-6}$ cycloalkyl and aryl; and R$_8$ and R$_9$ are independently selected from the group of —H, —C$_{1-6}$ alkyl, and —C$_{1-6}$ alkylsubstituted alkyl.

2. The compound as claimed in claim 1, wherein a is 1.

3. The compound as claimed in claim 1, wherein R$_1$ is —C(O)CH$_2$C(CH$_3$)$_2$COOH.

4. The compound as claimed in claim 2, wherein R$_1$ is —C(O)CH$_2$C(CH$_3$)$_2$COOH.

5. The compound, including pharmaceutically acceptable salts thereof, which is:

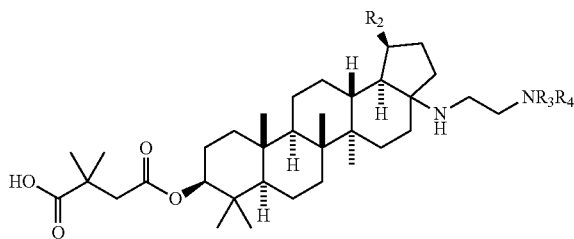

wherein R$_2$ is selected from the group of —H, methyl, isopropenyl and isopropyl; and R$_3$ and R$_4$ are independently selected from the group of —H, —C$_{1-6}$ alkyl, —C$_{1-6}$ alkylsubstituted alkyl and —C$_{3-6}$ cycloalkyl.

6. A compound which is selected from:

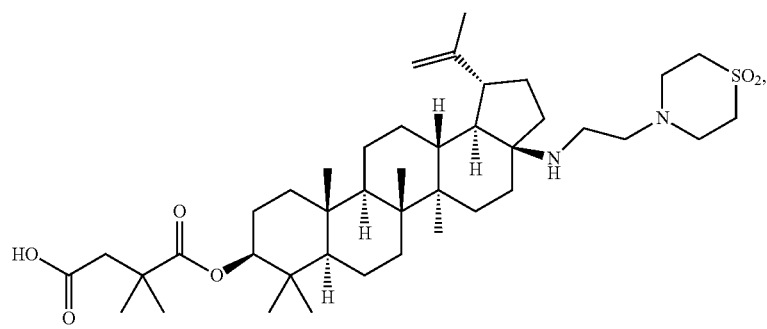

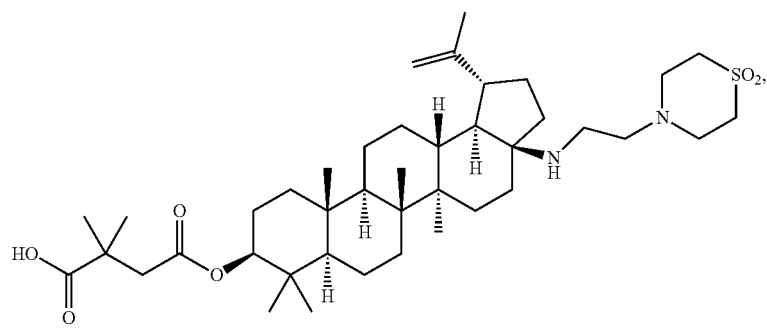

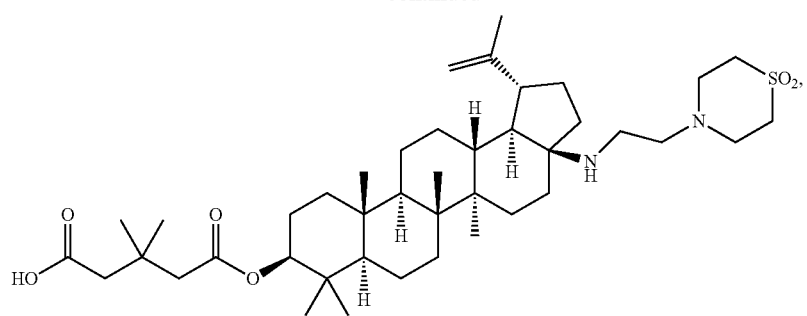
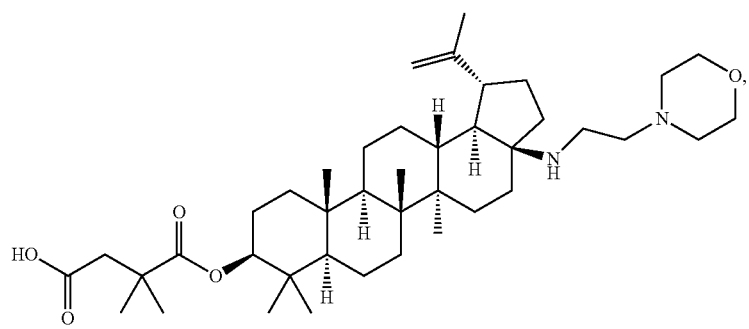
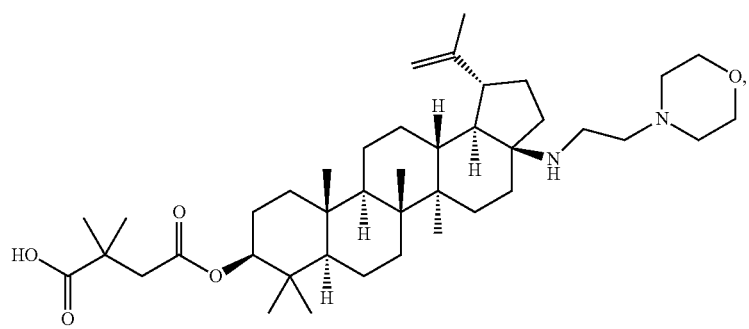
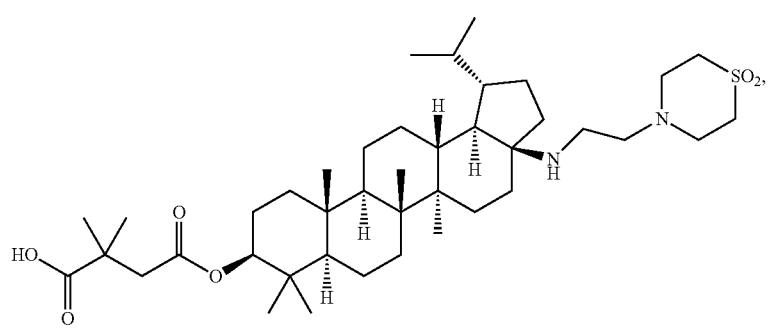
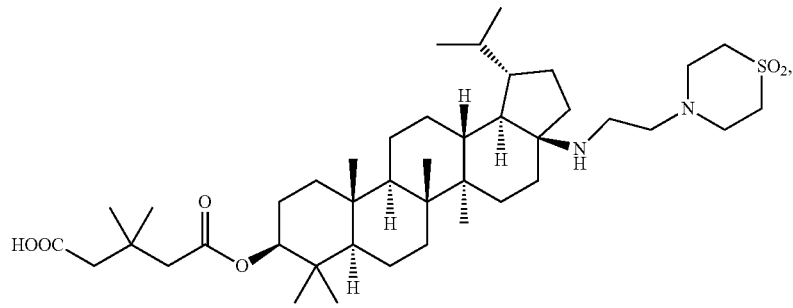

-continued

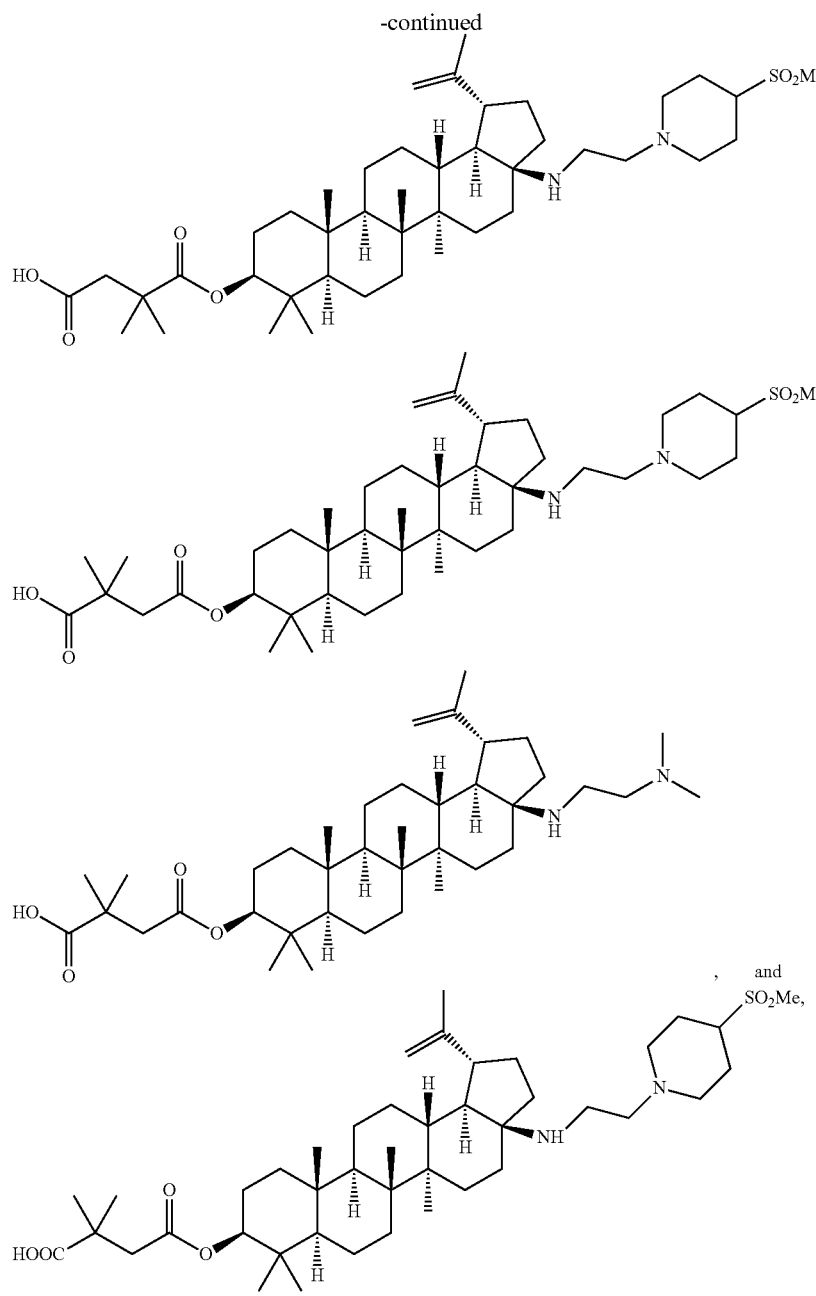

including pharmaceutically acceptable salts thereof.

7. A pharmaceutical composition which comprises an HIV ameliorating amount of one or more of the compounds as claimed in claim 1, together with one or more pharmaceutically acceptable carriers, excipients or diluents.

8. A pharmaceutical composition which comprises an HIV ameliorating amount of one or more of the compounds as claimed in claim 5, together with one or more pharmaceutically acceptable carriers, excipients or diluents.

9. A pharmaceutical composition which comprises an HIV ameliorating amount of one or more of the compounds as claimed in claim 6, together with one or more pharmaceutically acceptable carriers, excipients or diluents.

10. The pharmaceutical composition of claim 7, useful for ameliorating infection by HIV, which additionally comprises an HIV ameliorating amount of an AIDS treatment agent selected from the group consisting of: (a) an AIDS antiviral agent; (b) an anti-infective agent; (c) an immunomodulator; and (d) another HIV entry inhibitor.

* * * * *